US010568974B2

(12) United States Patent
Rogers et al.

(10) Patent No.: US 10,568,974 B2
(45) Date of Patent: Feb. 25, 2020

(54) ANIMAL MODELS OF ATHEROSCLEROSIS

(71) Applicant: Exemplar Genetics, LLC, Sioux Center, IA (US)

(72) Inventors: Christopher S Rogers, North Liberty, IA (US); John R Swart, Orange City, IA (US)

(73) Assignee: EXEMPLAR GENETICS LLC, Sioux Center, IA (US)

( * ) Notice: Subject to any disclaimer, the term of this patent is extended or adjusted under 35 U.S.C. 154(b) by 0 days.

(21) Appl. No.: 13/624,967

(22) Filed: Sep. 23, 2012

(65) Prior Publication Data

US 2013/0203870 A1 Aug. 8, 2013

Related U.S. Application Data

(63) Continuation-in-part of application No. 13/368,312, filed on Feb. 7, 2012, now abandoned.

(51) Int. Cl.
*A01K 67/027* (2006.01)
*A61K 49/00* (2006.01)

(52) U.S. Cl.
CPC ...... *A61K 49/0006* (2013.01); *A01K 67/0276* (2013.01); *A01K 2217/075* (2013.01); *A01K 2227/108* (2013.01); *A01K 2267/0362* (2013.01)

(58) Field of Classification Search
CPC .......... A01K 2300/00; A01K 2227/108; A01K 2217/075; A01K 2267/03; A01K 2217/052; A01K 67/0275; A01K 67/0276; C12N 15/8509; C12N 15/85; C12N 15/86; C12N 15/8778; A61D 19/04
See application file for complete search history.

(56) References Cited

U.S. PATENT DOCUMENTS

| | | | | |
|---|---|---|---|---|
| 5,464,764 | A * | 11/1995 | Capecchi et al. | 435/6.14 |
| 7,989,675 | B2 * | 8/2011 | Welsh et al. | 800/3 |
| 8,546,643 | B2 * | 10/2013 | Bentzon | A01K 67/0271 800/17 |
| 8,618,352 | B2 * | 12/2013 | Welsh | A01K 67/0278 435/325 |
| 2003/0208785 | A1 | 11/2003 | Tzang et al. | |
| 2009/0235368 | A1 * | 9/2009 | Welsh et al. | 800/3 |
| 2012/0220037 | A1 | 8/2012 | Fahrenkrug et al. | |

FOREIGN PATENT DOCUMENTS

| | | | |
|---|---|---|---|
| JP | 2013118859 | | 6/2013 |
| WO | 2006/111757 | A2 | 10/2006 |
| WO | WO 2008/106982 | * | 9/2008 |

OTHER PUBLICATIONS

Ishibashi et al J Clin Invest 92 (2), 883-93, 1993).*
Dai Nature Biotech., Mar. 2002, vol. 20, 251-255).*
Lai (Science, 2002, vol. 295, No. 1089, 1089-1092.*
Rogers J. Clin. Investigation, 2008, 118, 1571-1577.*
Sun J. Clin. Investigation, Apr. 2008, vol. 118, No. 4, p. 1578-1583.*
Stice et al (Therigeneology, 1998, 49: 129-138).*
Yanagimach et al Molecular and Cellular Endocrinology, 2002, 187, 241-248.*
Banki et al The Journal of Biological Chemistry, 1994, 2847-2851.*
Davis, B. et al., Swine In Biomedical Research Conference S2-9 (Year: 2011).*
Li et al Cellular reprogramming, 15, 1, 35-42 (Year: 2013).*
Hua et al Polish Journal of Veterinary Sciences vol. 19, No. 1 205-212 (Year: 2016).*
Lai et al Science, 295, 1089-1092 (Year: 2002).*
Lai et al Cloning ad Stem Cells, 5(4), 233-241 (Year: 2003).*
Al-Mashhadi et al Science Transnational Medicine, 5(166) 1-10 (Year: 2013).*
Volume 126, Issue 21 Supplement; Nov. 20, 2012 / Abstracts From the American Heart Association 2012 Scientific Sessions and Resuscitation Science Symposium (available at: http://circ.ahajournals.org/cgi/content/meeting_abstract/126/21_MeetingAbstracts/A14053).
Groenen et al., Analyses of pig genomes provide insight into porcine demography and evolution, Nature, Nov. 15, 2012; 491(7424):393-398; See, Supplement 1 at p. 14.
Hobbs et al., The LDL Receptor Locus in Familial Hypercholesterolemia: Mutational Analysis of a Membrane Protein, Annual Review of Genetics, 1990, pp. 133-170, vol. 24.
Mazur et al., A novel porcine model of atherosclerosis, FASEB Journal, 2006, p. A207, vol. 20, No. 4.
Whyte et al., Vascular endothelium-specific overexpression of human catalase in cloned pigs, Transgenic Research, 2011, pp. 989-1001, vol. 20, No. 5.
Davis, B. et al., "Targeted disruption of porcine LDLR: developing a model of hypercholesterolemia and atherosclerosis", Swine In Biomedical Research Conference 2011, S2-9.

* cited by examiner

*Primary Examiner* — Anoop K Singh
(74) *Attorney, Agent, or Firm* — Intrexon Corporation; Patrick J. Farley

(57) ABSTRACT

The present invention provides transgenic, large non-human animal models of atherosclerosis and hypercholesterolemia, as well as methods of using such animal models in the identification and characterization of therapies for atherosclerosis and hypercholesterolemia.

8 Claims, 13 Drawing Sheets
(4 of 13 Drawing Sheet(s) Filed in Color)

Specification includes a Sequence Listing.

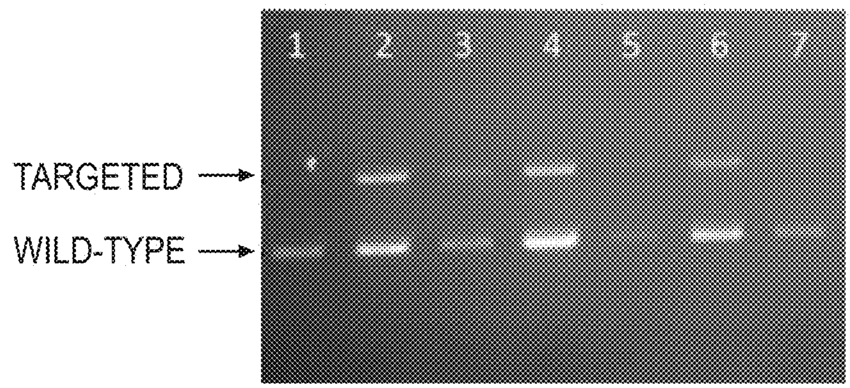
FIG. 3b
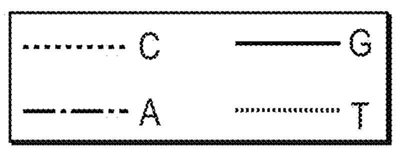
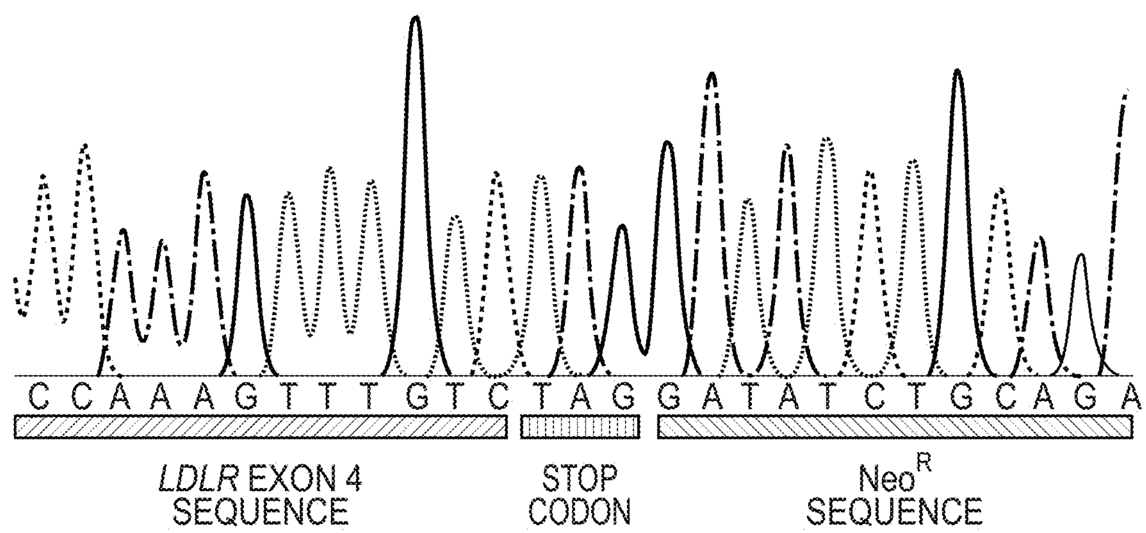
FIG. 3c

TABLE 1. SUMMARY OF *LDLR* GENE TARGETING AND SCNT ACTIVITY

| | GENE TARGETING EFFICIENCY[a] | NUMBER OF TRANSFERS | EMBRYOS PER TRANSFER (AVERAGE) | PREGNANCY RATE[b] | LIVE PIGS/LITTER | TOTAL LIVE BORN | LONG-TERM SURVIVAL[c] |
|---|---|---|---|---|---|---|---|
| MALE | 1.8% | 10 | 130 | 50% | 4.8 | 24 | 19 (79%) |
| FEMALE | 6.5% | 8 | 122 | 50% | 8.3 | 33 | 26 (79%) |

[a] GENE TARGETING EFFICIENCY REPORTED AS PERCENTAGE OF $G418^R$ CLONES THAT WERE PROPERLY TARGETED.

[b] PREGNANCY RATE REFERS TO FULL-TERM GESTATION.

[c] LONG-TERM SURVIVAL REFERS TO PIGS THAT ARE CURRENTLY ALIVE AND AVAILABLE FOR HERD PROPAGATION.

*FIG. 7*

```
                1                                                 50
hLDLR    (1)   MGPWGWKLRWTVALLLAAAGTAVGDRCERNEFQCQDGKCISYKWVCDGSA
pLDLR    (1)   MKSTGWVLRWAVALLIAAVAAAVEEMCGRNEFQCRDGKCISYKWICDGNT
               51                                               100
hLDLR   (51)   ECQDGSDESQETCLSVTCKSGDFSCGGRVNRCIPQFWRCDGQVDCDNGSD
pLDLR   (51)   ECKDGSDESLETCMSVTCKIGDFSCGGRVNRCIPESWRCDGQQDCENGSD
               101                                              150
hLDLR  (101)   EQGCPPKTCSQDEFRCHDGKCISRQFVCDSDRDCLDGSDEASCPVLTCGP
pLDLR  (101)   EEGCSPKTCSQDEFRCQDGKCIAPKFVCDSDRDCLDGSDEASCPTPTCGP
               151                                              200
hLDLR  (151)   ASFQCNSSTCIPQLWACDNDPDCEDGSDEWPQRCRGLYVFQGDSS--PCS
pLDLR  (151)   ASFQCNSSTCIPELWACDGDPDCEDGSDEWPQHCRSHSSSLPERSNNPCS
               201                                              250
hLDLR  (199)   AFEFHCLSGECIHSSWRCDGGPDCKDKSDEENCAVATCRPDEFQCSDGNC
pLDLR  (201)   ALEFHCHSGECIHSSWRCDGDTDCKDKSDEENCDVATCRPDEFQCSDGTC
               251                                              300
hLDLR  (249)   IHGSRQCDREYDCKDMSDEVGCVNVTLCEGPNKFKCHSGECITLDKVCNM
pLDLR  (251)   IHGSRQCDREYDCKDMSDEQGCVNATLCEGPNKFKCQSGECISLDKVCNS
               301                                              350
hLDLR  (299)   ARDCRDWSDEPIKECGTNECLDNNGGCSHVCNDLKIGYECLCPDGFQLVA
pLDLR  (301)   VRDCRDWSDEPLKECGTNECLDNKGGCSHICNDLKIGYECLCPEGFQLVD
               351                                              400
hLDLR  (349)   QRRCEDIDECQDPDTCSQLCVNLEGGYKCQCEEGFQLDPHTKACKAVGSI
pLDLR  (351)   KHRCEDIDECQDPDACSQICVNLEGSYKCQCEEGFQLEPLTKACKAIGTI
               401                                              450
hLDLR  (399)   AYLFFTNRHEVRKMTLDRSEYTSLIPNLRNVVALDTEVASNRIYWSDLSQ
pLDLR  (401)   AYLFFTNRHEVRKMTLDRSEYTSLIPNLKNVVALDTEVASNRIYWSDLSQ
               451                                              500
hLDLR  (449)   RMICSTQLDRAHGVSSYDTVISRDIQAPDGLAVDWIHSNIYWTDSVLGTV
pLDLR  (451)   RKIYSTQIDRAPSFSSYDTIIGEDLQAPDGLAVDWIHSNIYWTDSILGTV
               501                                              550
hLDLR  (499)   SVADTKGVKRKTLFRENGSKPRAIVVDPVHGFMYWTDWGTPAKIKKGGLN
pLDLR  (501)   SVADTKGVKRKTLFQEKGSKPRAIVVDPVHGFMYWTDWGTPAKIKKGGLN
               551                                              600
hLDLR  (549)   GVDIYSLVTENIQWPNGITLDLLSGRLYWVDSKLHSISSIDVNGGNRKTI
pLDLR  (551)   GVDVYSLVTEDIQWPNGITLDLSGGRLYWVDSKLHSISSIDVNGGNRKTV
               601                                              650
hLDLR  (599)   LEDEKRLAHPFSLAVFEDKVFWTDIINEAIFSANRLTGSDVNLLAENLLS
pLDLR  (601)   LEDKTKLAHPFSLAIFEDKVFWTDIINEAIFSANRLTGSDIHLMAENLLS
               651                                              700
hLDLR  (649)   PEDMVLFHNLTQPRGVNWCERTTLSNGGCQYLCLPAPQINPHSPKFTCAC
pLDLR  (651)   PEDIVLFHNLTQPRGVNWCERTALQNGGCQYLCLPAPQINPRSPKFTCAC
               701                                              750
hLDLR  (699)   PDGMLLARDMRSCLTEAEAAVATQETSTVRLKVSSTAVRTQHTTTRPVPD
pLDLR  (701)   PDGMLLAKDMRSCLTETEPAGTTQGPS----MVNSTAVGPKHT-------
               751                                              800
hLDLR  (749)   TSRLPGATPGLTTVEIVTMSHQALGDVAGRGNEKKPSSVRALSIVLPIVL
pLDLR  (740)   -------ASSELTTAESVTMSQHALGDVAGRGVTEKPQSVGALYIVLPIAL
               801                                              850
hLDLR  (799)   LVFLCLGVFLLWKNWRLKNINSINFDNPVYQKTTEDEVHICHNQDGYSYP
pLDLR  (784)   ILLLFFGTFLLWKNWRLKSINSINFDNPVYQKTTEDEVHICRSQDGYTYP
               851        862
hLDLR  (849)   SRQMVSLEDDVA
pLDLR  (834)   SRQMVSLEDDVA
```

*FIG. 8*

A.
Total Cholesterol (mg/dl)
600
400
200
0
LDLR+/+
LDLR+/-
LDLR-/-
*
B.
LDL (mg/dl)
500
400
300
200
100
0
LDLR+/+
LDLR+/-
LDLR-/-
*
C.
HDL (mg/dl)
40
30
20
10
0
LDLR+/+
LDLR+/-
LDLR-/-
*
D.
VLDL (mg/dl)
60
40
20
0
LDLR+/+
LDLR+/-
LDLR-/-
*
* p<0.05

A.
+/+ +/- -/-
targeted
wild-type
B.
+/+ +/- -/-
LDLR
+/+ +/- -/-
NeoR
targeted
wild-type
C.
+/+ +/- -/-
*
LDLR
GAPDH
D.
+/+ +/- -/-
1 2 3 4 5
1 2 3 5
1 2 5
E.
+/+ +/- -/-
LDLR
β-tubulin

ANIMAL MODELS OF ATHEROSCLEROSIS

CROSS REFERENCE TO RELATED APPLICATIONS

This application is a continuation-in-part application of U.S. application Ser. No. 13/368,312, filed on Feb. 7, 2012, which is hereby incorporated by reference in its entirety.

STATEMENT AS TO FEDERALLY SPONSORED RESEARCH

This invention was made with government support under grant number HL102950 awarded by the National Institutes of Health and the National Heart, Lung and Blood Institute. The government has certain rights to this invention.

SEQUENCE LISTING

The instant application contains a Sequence Listing which has been submitted in ASCII format via EFS-Web and is hereby incorporated by reference in its entirety. Said ASCII copy, created on Jan. 24, 2012, is named EXEM0003.txt and is 35,414 bytes in size.

FIELD OF THE INVENTION

This invention relates to transgenic, non-human animal models of disease, cells that can be used to make such animals, and methods of using these animals and cells.

BACKGROUND OF THE INVENTION

Many human diseases and conditions are caused by gene mutations. Substantial effort has been directed towards the creation of transgenic animal models of such diseases and conditions to facilitate the testing of approaches to treatment, as well as to gain a better understanding of disease pathology. Early transgenic animal technology focused on the mouse, while more recent efforts, which have been bolstered by the development of somatic cell nuclear transfer (SCNT), have included larger animals, including pigs, cows, and goats. This technology has resulted in the production of, for example, pigs in which the gene encoding α-1,3-galactosyltransferase has been knocked out, in efforts to generate organs that can be used in xenotransplantation (see, e.g., Lai et al., Science 295:1089-1092, 2002). Further, this technology has resulted in the production of CFTR−/− and CFTR-ΔF508/ΔF508 pigs (see, e.g., U.S. Pat. No. 7,989,675 and U.S. patent application Ser. No. 12/283,980). Additional applications of this technology include the production of large quantities of human proteins (e.g., therapeutic antibodies; see, e.g., Grosse-Hovest et al., Proc. Natl. Acad. Sci. U.S.A. 101(18):6858-6863, 2004). Substantial benefits may be obtained by the use of somatic cell nuclear transfer technology in the production of large animal models of human disease.

One example of a condition caused in part by a genetic mutation is hypercholesterolemia. Hypercholesterolemia is a metabolic derangement indicated by the presence of high levels of cholesterol in the blood. Elevated cholesterol in the blood is due to abnormalities in the levels of lipoproteins, the particles that carry cholesterol in the bloodstream. Familial hypercholesterolemia results from mutations in the low-density lipoprotein receptor and can lead to premature or early onset atherosclerosis.

Thus, another example of a disease caused in part by a genetic mutation is atherosclerosis, also known as arteriosclerotic vascular disease or ASVD. As stated above, atherosclerosis results from longstanding elevation of serum cholesterol, a condition that is associated with hypercholesterolemia. Atherosclerosis is the primary cause of cardiovascular disease, which is the most common cause of death in the United States. See, e.g., Chart www.nhlbi.nih.gov/resources/docs/cht-book.htm. Atherosclerosis is characterized by the accumulation of lipids, cholesterol, calcium deposits, and cellular debris in vessel walls. This results in plaque formation, arterial obstruction, and diminished blood flow to organs. In time, these plaques can rupture and lead to thrombosis, resulting in myocardial infarction, stroke, or death. The main risk factors include elevated lipid levels, hypertension, and diabetes. While these factors are heavily influenced by diet and lifestyle, there are also genetic determinants that influence the disease.

More than 11 million Americans have atherosclerosis. Current treatment strategies for atherosclerosis are directed at changing patient lifestyle and/or diet and decreasing cholesterol in a patient via pharmacological methods. Surgical interventions such as balloon angioplasty and stent placement are used for advanced cases of the disease. While these therapeutic approaches have benefited many patients with this disease, they are far from ideal.

As the baby boomer generation ages, the American Heart Association projects heart disease deaths to increase 2.5 times faster than the population, and the prevalence of heart disease is projected to increase by 16% each decade. See, e.g., Lloyd-Jones, D et al., Circulation 121 (7), 948-54, 2010. The estimated annual financial impact of cardiovascular disease in the U.S. today is $475 billion. Pharmaceutical companies invest over $8 billion per year in cardiovascular research, and federal funding accounts for an additional $2 billion annually. Yet, despite these significant expenditures, current treatments remain inadequate because therapeutic strategies that show promise in the current model systems fail to yield results in patients. See, e.g., Hackam, D. G. et al., JAMA, 296 (14), 1731-2, 2006. This lack of predictive efficacy in the drug development process is costly, with over 70% of all drug development costs being the result of failed drugs.

Drug development using inappropriate animal models and translating those therapies to patients is inefficient and extremely costly. The lack of an appropriate animal model that accurately replicates one or more of the manifestations of human atherosclerosis has been a major barrier to the development of effective therapies, interventions, and diagnostic tools for this deadly disease. Several mouse models have been generated with mutations in genes important for lipoprotein metabolism. While these models have been informative, they fall short of being reliable predictive models for the study of atherosclerosis in humans because, among other things, mice fail to develop the complex atherosclerotic lesions that are typical of the human disease.

Atherosclerosis and hypercholesterolemia are associated with elevated low-density lipoprotein (LDL), which results, in part, from mutations in the low-density lipoprotein receptor (LDLR). The LDLR is a cell-surface glycoprotein found mainly in the liver that plays an important role in maintaining proper homeostasis of blood cholesterol. Upon ligand binding, the receptor-lipoprotein complex is endocytosed and trafficked to the endosome where an acidic environment causes the release of the LDL. The empty receptor is then recycled to the cell surface. The LDL is metabolized and excess cholesterol is excreted.

In contrast to mice, the physiology and anatomy of the porcine cardiovascular system closely resembles that of humans. In fact, pigs have been used as models of cardiovascular disease, and pigs with naturally occurring mutations in their LDLR gene, and therefore possessing elevated LDL, have been reported. See, e.g., Grunwald, K. A et al., J Lipid Res 40 (3), 475-85, 1999; Hasler-Rapacz, J et al., Am J Med Genet 76 (5), 379-86, 1998; Rapacz, J et al., Science 234 (4783), 1573-7, 1986. These naturally occurring mutations in the LDL receptor do not destroy its function; rather they decrease binding affinity for plasma LDL. Even on a normal diet, these pigs develop severe cardiovascular disease and provide the first animal model to develop spontaneous hypercholesterolemia and atherosclerotic lesions ranging from fatty streaks to advanced plaques, with accompanying calcification, hemorrhage, and rupture.

Although pigs with naturally occurring mutations in the LDLR gene are an attractive model for hypercholesterolemia and atherosclerosis, there are significant drawbacks. First, there has been substantial variability in the plasma cholesterol levels and disease development. This is likely due to the mild nature of the mutation and the broad, uncharacterized genetic background of these animals. In contrast, pigs with genetically engineered mutations in the LDLR gene, such as "null" mutations (for example, LDLR +/− and LDLR −/−), or any of the more than 1000 LDLR mutations identified in humans, will provide a much more consistent, predictable and reliable model for disease progression and development. Using the techniques described in the present invention, any one or more of the mutations in the LDLR gene could be created and studied in a large animal model. Second, the limited availability of pigs with a natural occurring mutation in the LDLR gene has prevented broader access by the research community. Finally, because the pronounced atherosclerotic lesions typically take 3-4 years to develop and these pigs are from a very large, domestic pig breed, the study of these animals is difficult and expensive.

A large animal model that accurately replicates the manifestations of human hypercholesterolemia and atherosclerosis and shares similarities to humans in size, anatomy, physiology, and genetics would be a transformative resource in bridging the substantial gap between models currently used for early-stage drug discovery and Phase 0/I human clinical trials. Furthermore, there is great interest in advancing medical devices, interventional strategies, and non-invasive diagnostic methods beyond their current state, but these fields are also limited by the current models systems. Rodent models are not well suited for most of these applications due to their size, and domestic pigs fed high cholesterol diets are excessively large, difficult to house and handle, and suffer from significant variability in phenotype. See, e.g., Daugherty, A., Mouse models of atherosclerosis. Am J Med Sci, 323 (1), 3-10 (2002). An LDLR-deficient miniature pig would benefit multiple disciplines within the cardiovascular disease community. Therefore, in one aspect of the invention, the transgenic animal model is a new model for hypercholesterolemia and atherosclerosis in a miniature pig breed. In one embodiment, the present invention accomplishes this in two steps by combining gene targeting and SCNT.

SUMMARY OF THE INVENTION

The invention provides large, non-human animal models of human diseases or conditions, in which one or more genes associated with the diseases or conditions include one or more targeted mutations. The animals of the invention can be, for example, ungulates such as, e.g., pigs, cows, sheep, and goats. In one example, the disease or condition is atherosclerosis and the gene including one or more mutations is the low-density lipoprotein receptor (LDLR) gene.

The animal models of the invention can include the mutation(s) in one or both alleles of the LDLR gene in the genome of the transgenic animal, and the mutation(s) can result in full or partial inactivation of the gene(s). In one example, the mutation includes an insertion of an exogenous nucleic acid molecule and/or a transcription/translation termination sequence. In another example, the mutation substantially eliminates expression of a functional gene product of the targeted gene in cells in which such expression normally takes place, absent the mutation. In the case of an animal with a mutation or mutations in both alleles of a gene, the mutation or mutations in each allele can be identical to one another or can be different.

The animal models of the invention may also include a homologous transgenic copy of a wild-type or mutated gene from a different animal. In one embodiment, the invention may include an orthologous gene from a different animal. The animal models may thus include, for example, in addition to a mutation/inactivation of an endogenous gene, an inserted copy of a corresponding gene from another species. Thus, for example, an animal (such as a pig) in which an endogenous LDLR gene is mutated or inactivated may be modified to include a LDLR gene from another animal (such as a human), which may be wild-type or may include a mutation. The invention therefore provides transgenic, large (non-human) animal models of human diseases and conditions (e.g., pigs) in which one or more endogenous genes associated with the disease or condition are knocked-out (i.e., genetically altered in such a way as to inhibit the production or function of the product or gene) and replaced with a homologous wild-type or mutated gene derived from a different animal (e.g., a human). In one example, a pig with its endogenous porcine LDLR gene knocked-out expresses a human transgene encoding the LDLR gene or a mutation thereof.

The invention also provides isolated cells of transgenic, large non-human animal models of human diseases or conditions, in which one or more genes associated with the diseases or conditions include one or more targeted mutations. The animals can be, for example, ungulates, such as, e.g., pigs, cows, sheep, and goats. In one example, the disease or condition is atherosclerosis and the gene including one or more mutations is a low-density lipoprotein receptor gene.

Examples of LDLR mutations that can be included in the animals and cells of the present invention can include mutations affecting the synthesis of the receptor in the endoplasmic reticulum (ER), mutations that prevent proper transport of the receptor to the Golgi body, mutations that stop the binding of LDL to the receptor, mutations that inhibit the internalization of the receptor-ligand complex, and mutations that give rise to receptors that cannot recycle properly.

The cells of the invention can include the mutation(s) in one or both alleles of the genes in the genomes of the cells, and the mutation(s) can results in full or partial inactivation of the gene(s). In one example, the mutation includes an insertion of an exogenous nucleic acid molecule and/or a transcription/translation termination sequence. In another example, the mutation substantially eliminates expression of a functional gene product of the targeted gene in cells in which such expression normally takes place, absent the mutation. In the case of a cell with a mutation or mutations in both alleles of a gene, the mutation or mutations in each allele can be identical to one another or can be different. In one example, the cells are fetal cells, such as fetal fibroblasts. Additional examples of cell types included in the invention are provided below.

The invention further provides methods of making transgenic, large non-human animal models of diseases or conditions as described above and elsewhere herein. The methods can include the steps of: (i) introducing one or more mutations into an allele of one or more genes associated with a disease or condition in a cell (e.g., a fetal fibroblast) to generate a donor cell; (ii) introducing the nucleus of the donor cell into a recipient cell (e.g., an enucleated oocyte) to generate an embryo; and (iii) transferring the embryo into a surrogate female. The animals can be, for example, ungulates, such as, e.g., pigs, cows, sheep, and goats. In one example, the disease or condition is hypercholesterolemia or atherosclerosis and the gene including one or more mutations is a LDLR gene. In a variation of these methods, the donor cell includes one or more mutations in one allele of a gene, and the method is carried out to introduce one or more mutations into the other allele. In another example, the methods further involve breeding an animal that is born from the surrogate female to obtain a homozygous mutant.

The invention also includes methods of identifying therapeutic agents that can be used in the treatment of diseases or conditions (e.g., the diseases of hypercholesterolemia and atherosclerosis). These methods involve administering one or more candidate therapeutic agents to a transgenic animal, as described above, and monitoring the animal for one or more symptoms of the disease or condition. Detection of improvement or other change in a symptom of the disease or condition indicates the identification of a compound that may be used in the treatment or prevention of the disease or condition.

The invention also includes methods of providing surgical training and medical imaging that can be used in the treatment of diseases or conditions (e.g., the diseases of hypercholesterolemia and atherosclerosis). These methods involve using the transgenic animals of the present invention for the refinement of surgical techniques using standard approaches, as well as minimally invasive and robotic technologies. In the context of medical imaging, new and improved technologies including noninvasive imaging could be evaluated using instrumentation designed for humans.

The invention further provides methods of targeting the introduction of mutations into pig cells. These methods involve the steps of providing pig cells (e.g., fetal fibroblasts), using an adeno-associated viral vector to deliver a gene targeting construct to the isolated pig cells, in the absence of cell detachment and reattachment, and selecting gene-targeted clones. The cells are in culture for 30 days or less (e.g., 20 days or less in the Examples) during the targeting construct delivery and selection steps. These methods can be used, for example, for the introduction of a mutation into a low-density lipoprotein receptor gene in the pig cell. Information concerning other examples of mutations that can be used in the present invention, as well as the use of the present methods to inactivate or replace genes (e.g., to replace pig genes with human genes), is provided below.

By "donor cell" is meant a cell from which a nucleus or chromatin material is derived, for use in nuclear transfer. As is discussed elsewhere herein, nuclear transfer can involve transfer of a nucleus or chromatin only, as isolated from a donor cell, or transfer of an entire donor cell including such a nucleus or chromatin material.

By "genetic modification," "mutation," or "disruption" of a gene (e.g., a LDLR gene) is meant one or more alterations in gene sequences (including coding sequences and non-coding sequences, such as introns, promoter sequences, and 5' and 3'-untranslated sequences) that alter the expression or activity of this gene by, for example, insertion (of, e.g., heterologous sequences, such as selectable markers, and/or termination signals), deletion, frame shift mutation, silent mutation, nonsense mutation, missense mutation, point mutation, or combinations thereof. In one example, the amino acid sequence encoded by the nucleic acid sequence has at least one amino acid altered as compared to a naturally-occurring sequence. Examples of mutations include the insertion of a polynucleotide into a gene, the deletion of one or more nucleotides from a gene, and the introduction of one or more base substitutions into a gene. In one embodiment of the present invention, modifications of LDLR gene sequences are those that lead to one or more features or symptoms of hypercholesterolemia or atherosclerosis in transgenic animals including a mutation in, or disruption of, one of the LDLR alleles. In another embodiment of the present invention, modifications of LDLR gene sequences are those that lead to one or more features or symptoms of hypercholesterolemia or atherosclerosis in transgenic animals including a mutation in, or disruption of, both LDLR alleles. As is discussed elsewhere herein, the modifications in the two LDLR alleles of such animals can be identical or different. Further, the modifications can result in a complete lack of functional LDLR production, or can result in diminished functional LDLR production, as may be characteristic of less severe forms of the disease.

Examples of such mutations include but are not limited to (i) Class I mutations, which affect the synthesis of the receptor in the endoplasmic reticulum (ER) (for example, the Q12X mutation), (ii) Class II mutations, which prevent proper transport of the receptor to the Golgi body (for example, the G525D mutation), (iii) Class III mutations, which prevent the binding of LDL to the receptor (for example, the deletion of exons 2 and 3), (iv) Class IV mutations, which inhibit the internalization of the receptor-ligand complex (for example, the Y807C mutation), and (v) Class V mutations, which give rise to receptors that cannot recycle properly (for example, the E387K mutation). See, e.g., Hobbs et al. Annu Rev Genet. 1990, 24:133-170.]

In one example, a mutation is introduced by the insertion of a polynucleotide (for example, a positive selection marker, such as an antibiotic resistance gene (e.g., a neomycin resistance gene)) into an endogenous gene. Optionally, a mutation that is introduced into such an endogenous gene reduces the expression of the gene. If desired, the polynucleotide may also contain recombinase sites flanking the positive selection marker, such as loxP sites, so that the positive selection marker may be removed by a recombinase (e.g., cre recombinase).

By "homologous" genes is meant a pair of genes from two animal species that encode proteins having similar functional and physical properties. The proteins encoded by homologous genes are often very similar in structure and function (although not always), and typically have a common evolutionary origin. In one embodiment, the sequence identity is typically equal to or greater than 80%, equal to or greater than 90%, equal to or greater than 95%, or equal to or greater than 98% between two gene homologs. One example of a homologous gene pair is the porcine LDLR and human LDLR gene locus.

By "orthologous" genes or "orthologs" is meant genes that are separated by a speciation event wherein one ortholog may be substituted by genetic engineering into its corresponding gene in another species.

By animal "knock-out" is meant an animal (for example, a pig or mouse; also see other animals described herein) having a genome in which the function of a gene has been disrupted, or "knocked-out." A common method of producing disabled genes using recombinant DNA technology involves inserting an antibiotic resistance gene into the normal DNA sequence of a clone of the gene of interest by homologous recombination. This disrupts the action of the gene, thereby preventing it from leading to the production of an active protein product. A cell (or cell nucleus) in which this transfer is successful can be injected into a recipient cell (e.g., an enucleated oocyte) to generate a transgenic animal by nuclear transfer. In another approach, the cell is injected into an animal embryo, producing a chimeric animal. These animals are bred to yield a strain in which all of the cells contain the knocked-out gene.

By "heterozygous knock-out non-human mammal" is meant a mammal other than a human in which one of the two alleles of an endogenous gene (such as the LDLR gene) have been genetically targeted, or knocked out, resulting in a marked reduction or elimination of expression of a functional gene product, which is achieved by gene deletion or disruption.

By "homozygous knock-out non-human mammal" is meant a mammal other than a human in which the two alleles of an endogenous gene (such as the LDLR gene) have been genetically targeted, or knocked out, resulting in a marked reduction or elimination of expression of a functional gene product, which is achieved by gene deletion or disruption. According to the invention, the genetic targeting event at both alleles may or may not be the same. Thus, a non-human animal, in which the two alleles of an endogenous gene (such as a LDLR gene) have been genetically targeted by two different targeting vectors resulting in the null expression of the gene, would be considered as being a homozygous knock-out non-human mammal.

An example of a "knock-in mutation" is one resulting in the insertion of a mutation into an endogenous gene, for example, introducing the G525D or another mutation into a LDLR gene.

By "recipient cell" is meant a cell into which a donor cell, a donor cell nucleus, or donor cell chromatin is introduced. In one preferred embodiment, recipient cells are enucleated prior to nuclear transfer. Examples of recipient cells include oocytes, fertilized zygotes, and two-cell embryos.

By "transgenic, large non-human animal" is meant any non-human animal that includes a genetic modification, as defined herein. Examples of such animals include animals other than mice such as, for example, ungulates. Examples of ungulates that can be used in the invention include members of the orders Perissodactyla and Artiodactyla, such as any members of the family Suidae, and in particular any member of the genus *Sus*, such as *Sus scrofa*, which is also known as the domestic pig or a subspecies thereof (*Sus scrofa domestica*). Examples of *Sus scrofa domestica* breeds that can be used in the present invention include Landrace, Hampshire, Duroc, Chinese Meishan, Berkshire, Piĉtrain and Yorkshire. Examples of miniature pigs that can be used in the present invention include Ossabaw, Hanford, Sinclair, Libechov, Goettingen, Yucatan, Bama Xiang Zhu, Wuzhishan, and Xi Shuang Banna. In addition to porcines, additional ungulates that can be used in the invention include bovines, ovines, and caprines. Thus, for example, the invention can include the use of cows (e.g., *Bos taurus* or *Bos indicus*), sheep, goats, buffalos, antelopes, oxen, horses, donkeys, mule, deer, elk, caribou, water buffalo, camels, llama, alpaca, and elephants.

The invention provides several advantages over the state of the art, as it provides large, non-human animal models that can be used in the identification and characterization of therapies for genetic diseases. One example of such a disease is atherosclerosis, and conditions leading to atherosclerosis, such as hypercholesterolemia, which, as discussed above, is a devastating disease, leading to thrombosis, resulting in myocardial infarction, stroke, or death. In one embodiment, the pigs of the present invention exhibit at least a 10% increase in total cholesterol level in blood plasma as compared to non-genetically modified or wild-type pigs fed the same diet. In another embodiment, the pigs of the present invention exhibit at least a 30%, preferably at least 60%, preferably at least 90%, more preferably at least 100%, more preferably at least 120%, more preferably at least 130%, and more preferably at least 140% increase in blood plasma as compared to non-genetically modified or wild-type pigs fed the same diet.

Despite progress in understanding and treating atherosclerosis, the pathogenesis of the disease is still not well understood and current therapies remain inadequate. A major impediment to answering questions is the lack of an animal model that shows disease similar to that in humans. Availability of hypercholesterolemia and atherosclerosis pig models will allow investigators to address key problems that have persisted unresolved for years. As a result, it will be possible to develop new treatments, medical devices, therapies, and preventions.

Further, given the close physiological relationship between humans and large animals, such as pigs, there is an increased likelihood that results obtained using the animal models of the invention can be applied to humans, relative to other animal models. For example, the commonly used mouse models of cardiovascular disease fail to develop atherosclerotic lesions and vulnerable plaques that spontaneously rupture. This is likely due to genetic, biochemical, and physiological differences between mice and humans. Specifically with respect to pigs, it is noted that pigs and humans have anatomical, histological, biochemical, and physiologic similarities. Furthermore, pigs have long been studied as models of human cardiovascular disease, primarily due to their similarities of their cardiovascular systems and their more human-like size. The pig is the preferred animal for testing in the cardiovascular device industry. As an example, while spontaneous atherosclerosis in pigs is rare, when fed a diet high in saturated fat and cholesterol, pigs can develop atherosclerotic lesions similar to those seen in humans.

The invention thus can be used to provide substantial benefits in the treatment of diseases and conditions caused by or associated with gene mutations, such as familial hypercholesterolemia and atherosclerosis.

Other features and advantages of the invention will be apparent from the drawings, the detailed description, the experimental examples, and the claims.

BRIEF DESCRIPTION OF THE DRAWINGS

This patent application file contains at least one drawing executed in color. Copies of this patent application publication with color drawing(s) will be provided by the Office upon request and payment of the necessary fee.

FIG. 3 shows PCR screening results identified LDLR-targeted cells. FIG. 3C shows a sequence chromatogram of the site of LDLR disruption by the $NEO^R$ cassette. The engineered termination stop codon is noted.

FIG. 4 is a Southern blot of genomic DNA from LDLR-targeted pig fetuses (gestational day 35).

FIG. 5 is a Southern blot of genomic DNA from LDLR-targeted pigs.

FIG. 7 shows Table 1, which summarizes LDLR gene targeting and SCNT activity.

FIG. 8 shows an amino acid sequence alignment for human LDLR (hLDLR) (SEQ ID NO: 5) and porcine LDLR (pLDLR) (SEQ ID NO: 4).

FIG. 9A shows total cholesterol, FIG. 9B shows LDL cholesterol, FIG. 9C shows HDL cholesterol, FIG. 9D shows VLDL cholesterol, and FIG. 9E shows triglycerides. Error bars represent standard SEM.

FIG. 10A shows total cholesterol, FIG. 10B shows LDL cholesterol, FIG. 10C shows HDL cholesterol, and FIG. 10D shows VLDL cholesterol. Error bars represent SEM.

FIG. 12A shows a representative PCR genotyping gel. The presence of the $Neo^R$ cassette in the targeted allele results in the larger PCR product. FIG. 12B is a genomic Southern blot that confirms all 3 genotypes. The left shows hybridization of an LDLR probe and the right shows hybridization by the $Neo^R$ probe. Again, the targeted allele is larger due to the $Neo^R$ cassette. FIG. 12C is a representative northern blot showing that the targeted allele produces no normal LDLR mRNA. The asterisk (*) represents a minor mRNA species that is the full-length LDLR mRNA that contains the $Neo^R$ cassette. The bracket (}) indicates two minor mRNA species that are likely the result of nonsense-mediated mRNA altered splicing. This is confirmed by RT-PCR shown in FIG. 12D. Using PCR primers that amplify from exon 1 to exon 5, the targeted LDLR allele produces no normal mRNA, but does produce mRNA species with deletions of exon 4 or exons 3 and 4. This is seen in both the LDLR+/− and LDLR−/− pigs. This result was confirmed by DNA sequencing. FIG. 12E is a representative western blot that confirms that the LDLR−/− pigs produce no LDLR protein.

DETAILED DESCRIPTION OF THE INVENTION

Figure 1:
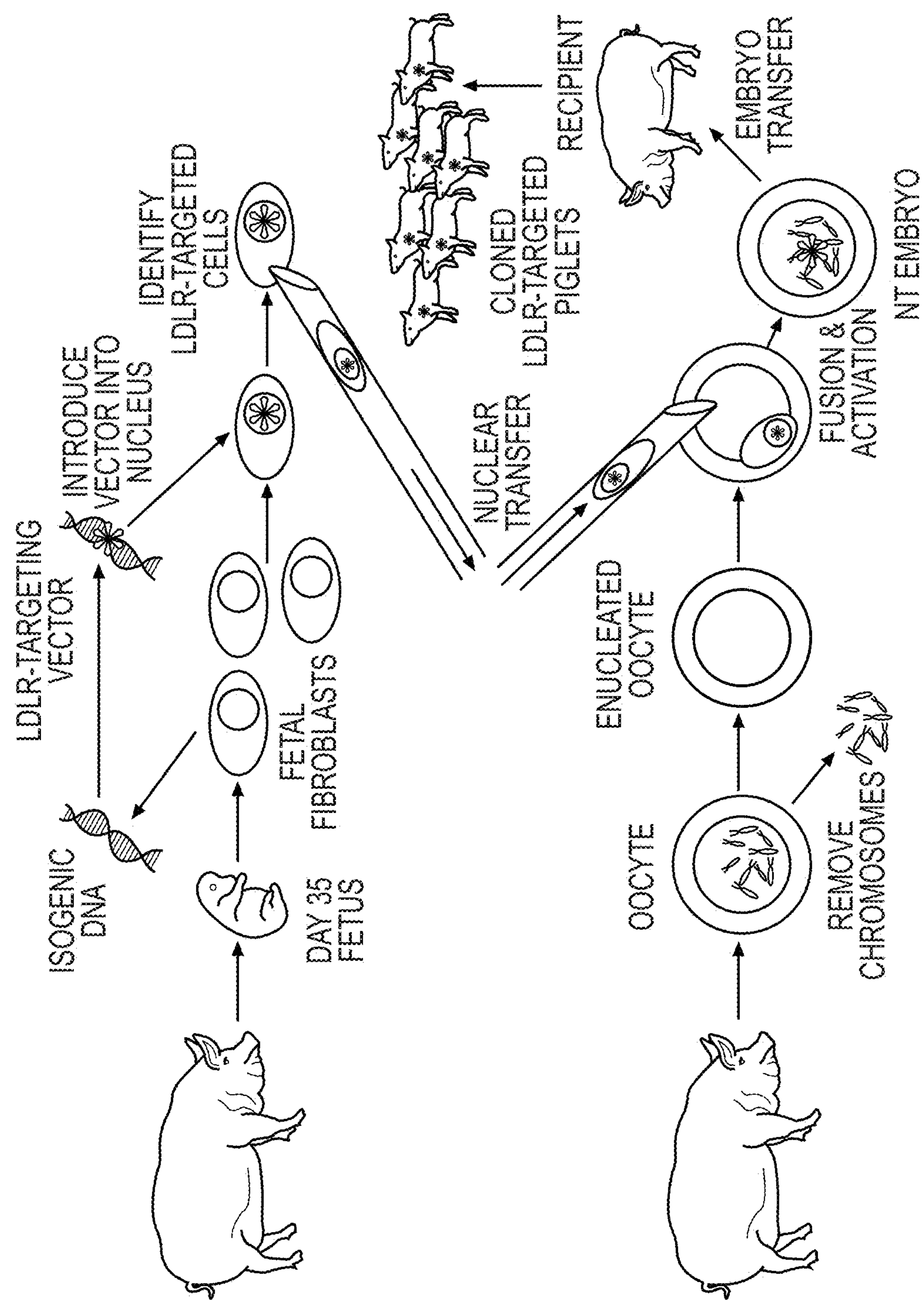
FIG. 1 is a schematic drawing showing one example of a method for generating LDLR-targeted pigs. Fibroblasts are obtained from day 35 Yucatan fetuses. The targeting vector (with, for example, a LDLR mutation indicated by the asterisk) is introduced to fetal fibroblasts via AAV infection. Properly targeted cells are identified by PCR and Southern blot. Following nuclear transfer and fusion and/or activation, nuclear transfer embryos are transferred to recipient animals. After a 114 day gestation period, the resulting piglets have one LDLR-targeted allele.

The invention provides animal models of human disease (e.g., atherosclerosis), which can be used in the identification and characterization of approaches for treating the diseases and conditions. As is discussed further below, the animal models of the invention are large, non-human animals, such as pigs, which have been genetically modified to include one or more mutations in a gene associated with a particular disease or condition, for example, the low-density lipoprotein receptor (LDLR) gene in hypercholesterolemia and atherosclerosis. The genetic modifications can result in the animals having one or more symptoms characteristic of the disease or condition. Animals exhibiting such symptoms are particularly advantageous in the development of therapeutic approaches, as candidate drugs and other approaches to treatment can be evaluated for effects on the symptoms in such animals. Thus, in addition to the animal models themselves, the invention also provides methods of using the animals for identifying and characterizing treatments.

Further, the invention includes methods of making transgenic, large non-human animal models and cells that can be used in these methods. The animal models systems, methods, and cells of the invention are described further, below.

In one embodiment, the invention provides a heterozygous or homozygous knock-out non-human mammal (e.g., a pig). In one example, the invention provides a pig with its endogenous porcine LDLR gene knocked-out (i.e., a LDLR+/− or LDLR−/− pig.)

In addition to animals including knock-outs or mutations in endogenous genes, the invention also includes transgenic, large non-human animal models of human diseases and conditions (e.g., pigs), in which one or more endogenous genes associated with the diseases or conditions are knocked-out (i.e., genetically altered in such way as to inhibit the production or function of the products of these genes) and replaced with a comparable wild-type or mutated gene derived from a different animal (e.g., a human). In one example, a pig with its endogenous porcine LDLR gene knocked-out, expresses a mutant human LDLR transgene, such as those described at www.ucl.ac.uk/ldlr/Current/index.php?select_db=LDLR. Alternatively, the human transgene may encode a normal, wild-type copy of a gene of interest (e.g., LDLR). These embodiments of the invention are especially useful for the generation of non-human animal models of human diseases and conditions that can be used to test existing and potential therapeutics that may only (or may preferentially) modulate or treat the disease when contacting, or being in the presence of, human copies of the disease gene or protein in question.

The invention is described herein in reference to animal models of hypercholesterolemia and atherosclerosis, which are generated by mutation, deletion or replacement of the LDLR gene. However, the methods of the invention are also applicable to the development of animal models of additional diseases and conditions.

The transgenic animals of the invention can be made using the following general strategy. Briefly, the genome of a cell (e.g., a fetal fibroblast) from an animal of interest, such as a pig, is genetically modified by, for example, gene targeting by homologous recombination, to create a "donor cell." According to the methods of the invention, the genetic modification results in at least partial inactivation of a gene associated with a particular disease or condition (e.g., a LDLR gene in hypercholesterolemia or atherosclerosis), as will be described in further detail below. The nucleus of such a genetically modified donor cell (or the entire donor cell, including the nucleus) is then transferred into a so-called "recipient cell," such as an enucleated oocyte. After activation and, typically, a brief period of in vitro culture, the resulting embryo is implanted into a surrogate female in which development of the embryo proceeds. This approach is illustrated with respect to pigs in FIG. 1. Typically, the donor cell, oocyte, and surrogate female are of the same species, but the sources can be different species, as is known in the art.

Details of methods for making large genetically modified animals, such as pigs, according to the invention, are provided below. Additional information concerning methods for making genetically modified pigs and other large animals is known in the art and can also be used in the present invention (see, e.g., U.S. Pat. No. 7,547,816; and WO 2005/104835; Prather et al., Reproductive Biology and Endocrinology 1:82, 1-6, 2003; Hao et al., Transgenic Res. 15:739-750, 2006; Li et al., Biology of Reproduction 75:226-230, 2006; Lai et al., Nature Biotechnology 24(4): 435-436, 2006; Lai et al., Methods in Molecular Biology 254(2):149-163, 2004; Lai et al., Cloning and Stem Cells 5(4):233-241, 2003; Park et al., Animal Biotechnology 12(2):173-181, 2001; Lai et al., Science 295:1089-1092, 2002; Park et al., Biology of Reproduction 65:1681-1685, 2001; the contents of each of which are incorporated herein by reference).

The transgenic animals of the invention can be any non-human mammals, including, for example, ungulates. Examples of ungulates that can be used in the invention include members of the orders Perissodactyla and Artiodactyla, such as any members of the family Suidae, and in particular any member of the genus *Sus*, such as *Sus scrofa*, which is also known as the domestic pig or a subspecies thereof (*Sus scrofa domestica*). In one example, the animal is a Yucatan miniature swine. In addition to porcines, additional ungulates that can be used in the invention include bovines, ovines, and caprines. Thus, for example, the invention can include the use of cows (e.g., *Bos taurus* or *Bos indicus*), sheep, goats, buffalos, antelopes, oxen, horses, donkeys, mule, deer, elk, caribou, water buffalo, camels, llama, alpaca, and elephants.

The invention includes animals in which only one allele of a targeted gene (e.g., LDLR) is disrupted, with the other allele remaining unaffected. These animals, which are referred to herein as "heterozygous" or "hemizygous" animals, can be used, for example, as models to study the development or progression of a disease (for example, hypercholesterolemia or atherosclerosis) in heterozygous animals. Further, these animals can be used in breeding approaches to generate homozygous mutants, if desired, for example, in the case of diseases caused by homozygous recessive mutations.

The heterozygous animals of the present invention can also be used as animal models themselves, in the case of diseases caused by autosomal dominant mutations. For example, the heterozygous pigs of the present invention can be used to study the degree of hypercholesterolemia as compared to LDLR−/− pigs, the severity of coronary atherosclerosis as defined by percent stenosis, and the severity of aortic atherosclerosis as the percent of surface area with raised lesions. Based on the loss-of-function nature of the mutation in LDLR-targeted pigs, the severity of atherosclerosis is expected to be the greatest and time-of-onset the shortest in LDLR−/− pigs, followed by LDLR+/− pigs. This would be consistent with what is seen in humans with homozygous and heterozygous familial hypercholesterolemia.

Also included in the invention are homozygous mutant animals, in which both alleles of a target gene (e.g., LDLR) are disrupted or mutated, by the same or different mutations. In addition to being obtainable by breeding approaches involving hemizygous animals, homozygous mutant animals can also be obtained using an approach in which a cell (e.g., a fetal fibroblast) including a mutation in one allele, such as a cell obtained from an animal produced using the method summarized above, is subjected to gene targeting by homologous recombination to achieve modification of the remaining allele. The resulting donor cell can then be used as a source of a modified nucleus for nuclear transfer into a recipient cell, such as an enucleated oocyte, leading to the formation of a homozygous mutant embryo which, when implanted into a surrogate female, develops into a homozygous mutant animal.

A target gene (e.g., a LDLR gene) can be subject to genetic modification in any appropriate cell type of a species for which it is desired to create an animal model of a disease associated with mutation of the gene, according to the invention. As is understood in the art, it is necessary to be able to culture and carry out homologous recombination in a cell that is to be used as a donor cell. A particular example of such a cell, which is described in more detail below in connection with pigs, in the experimental examples, is the fetal fibroblast. These cells can be obtained using, for example, the approach described in U.S. Pat. No. 7,547,816 and other references cited herein.

The invention also includes the use of other cell types that may be present in the cell preparations obtained using the method described in U.S. Pat. No. 7,547,816. Additional examples of cells that can be used as donor cells in making the transgenic animals of the invention include other fetal cells, placental cells, or adult cells. Specific examples of such cells for gene targeting include differentiated cells such as fibroblasts, epithelial cells, neural cells, epidermal cells, keratinocytes, hematopoietic cells, melanocytes, chondrocytes, B-lymphocytes, T-lymphocytes, erythrocytes, macrophages, monocytes, placental, and muscle cells.

If a cell to be genetically altered is derived from an embryo or a fetus, the cell (e.g., a fetal cell or placental cell) can be isolated at any time during the gestation period until the birth of the animal, which may or may not be itself genetically altered. In the case of a pig, such cells can be obtained, for example, between 20 to 90 days of gestation, between 25 to 60 days of gestation, between 30 to 45 days of gestation, or between 35 to 40 (e.g., at 35 days) of gestation. The time periods for obtaining cells from other animals is known in the art (see, e.g., U.S. Pat. Nos. 7,420,099 and 7,928,285).

Gene targeting carried out to make the cells and animals of the invention can result in gene inactivation by disruption, removal, modification, or replacement of target gene sequences. For example, inactivation can take place by the insertion of a heterologous sequence and/or a stop codon into a target gene. A specific example of this type of inactivation, in the context of a LDLR gene, is described in the experimental examples, below. As is known in the art, inserted sequences can replace previously existing sequences in a gene or can be added to such sequences, depending on the design of the targeting construct. Also as is known in the art, the design of targeting constructs can be altered, depending upon whether it is desired to completely knock out the function of a gene or to maintain some level of reduced function. In the case of LDLR, for example, complete knock out of function would be consistent with the most severe, yet rare, forms of familial hypercholesterolemia and atherosclerosis in which there is no LDLR present. However, other less dramatic changes may be desirable for the generation of models of disease maintaining some LDLR function. These would include mutations in which some LDLR function is retained, such as in the heterozygous animals described above. Such changes may be achieved by, for example, replacement with sequences that are identical to wild-type sequences, except for the presence of specific mutations giving rise to features of the target disease. In other approaches, coding sequences are not altered or are minimally altered and, rather, sequences impacting expression of a target gene, such as promoter sequences, are targeted. In any case, selectable marker insertion is often desirable to facilitate identification of cells in which targeting has occurred. If desired, such markers or other inserted sequences can later be removed by, e.g., cre-lox or similar systems.

A "humanized" atherosclerotic model (LDLR−/− expressing a mutant human LDLR transgene) can be made numerous ways, including, but not limited to: i) introducing a mutant human LDLR cDNA, partial mutant human LDLR gene, or entire human LDLR gene carrying a mutation into pig LDLR−/− cells, selecting for mutant human LDLR gene insertion, and using these cells as nuclear donors in somatic cell nuclear transfer, and ii) introducing a mutant human LDLR cDNA, partial mutant human LDLR gene, or entire human LDLR gene carrying a mutation to pig LDLR−/− into matured oocytes, fertilizing, then transferring to a recipient female.

As is known in the art, targeted gene modification requires the use of nucleic acid molecule constructs having regions of homology with a targeted gene (or flanking regions), such that integration of the construct into the genome alters expression of the gene, either by changing the sequence of the gene and/or the levels of expression of the gene. Thus, to alter a gene, a targeting construct is generally designed to contain three main regions: (i) a first region that is homologous to the locus to be targeted (e.g., the LDLR gene or a flanking sequence), (ii) a second region that is a heterologous polynucleotide sequence (e.g., encoding a selectable marker, such as an antibiotic resistance protein) that is to specifically replace a portion of the targeted locus or is inserted into the targeted locus, and (iii) a third region that, like the first region, is homologous to the targeted locus, but typically is not contiguous with the first region of the genome. Homologous recombination between the targeting construct and the targeted wild-type locus results in deletion of any locus sequences between the two regions of homology represented in the targeting vector and replacement of that sequence with, or insertion into that sequence of, a heterologous sequence that, for example, encodes a selectable marker. Use of such promoters may not be required in cases in which transcriptionally active genes are targeted, if the design of the construct results in the marker being transcribed as directed by an endogenous promoter. Exemplary constructs and vectors for carrying out such targeted modification are described herein. However, other vectors that can be used in such approaches are known in the art and can readily be adapted for use in the invention.

In order to facilitate homologous recombination, the first and third regions of the targeting vectors (see above) include sequences that exhibit substantial identity to the genes to be targeted (or flanking regions). By "substantially identical" is meant having a sequence that is at least 80%, preferably at least 85%, preferably at least 90%, more preferably at least 95%, even more preferably at least 98%, and even more preferably 100% identical to that of another sequence. Sequence identity is typically measured using BLAST® (Basic Local Alignment Search Tool) or BLAST® 2 with the default parameters specified therein (see, Altschul et al., J. Mol. Biol. 215: 403-410, 1990; Tatiana et al., FEMS Microbiol. Lett. 174: 247-250, 1999). These software programs match similar sequences by assigning degrees of homology to various substitutions, deletions, and other modifications. Thus, sequences having at least 80%, preferably at least 85%, preferably at least 90%, more preferably at least 95%, even more preferably at least 98%, and even more preferably 100% sequence identity with the targeted gene loci can be used in the invention to facilitate homologous recombination.

The total size of the two regions of homology (i.e., the first and third regions noted above) can be, for example, approximately between 2-25 kilobases (for example, approximately between 4-20 kilobases, approximately between 5-15 kilobases, or approximately between 6-10 kilobases), and the size of the second region that replaces a portion of the targeted locus can be, for example, approximately between 0.5-5 kilobases (for example, approximately between 1-4 kilobases or approximately between 3-4 kilobases). In the case of pig LDLR, the targeting construct (SEQ ID NO: 3) can be designed based on the sequence shown in the enclosed Sequence Appendix (SEQ ID NO: 2). A specific example of such a construct is described below, in the experimental examples.

The targeting constructs can be included within any appropriate vectors, such as plasmid or viral vectors (e.g., adenovirus or adeno-associated virus (AAV) vectors), which can be introduced into cells using standard methods including, for example, viral transduction, electroporation, or microinjection. One preferred example of the invention, which is described in detail in the experimental examples, below, employs a recombinant adeno-associated viral vector (rAAV), which can be made by standard methods or produced commercially.

The use of AAV to deliver the targeting construct offers many benefits. First, AAV1 (and other AAV serotypes) infects pig fetal fibroblasts with 95-100% efficiency. Second, AAV infection of pig fetal fibroblasts results in little or no cell toxicity. Third, AAV infection results in the delivery of a single-stranded gene targeting construct directly to the nucleus. Single-stranded gene targeting vectors are thought to yield more efficient gene targeting and result in a more favorable homologous recombination to non-homologous recombination ratio (Hendrie and Russell, Molecular Therapy 12(1):9-17, 2005).

The methods of the invention, employing AAV vectors, resulted in high levels of gene targeting efficiency in these somatic cells, as compared to prior methods. Central to the methods of the invention is the fact that the entire procedure was performed in a time-sensitive manner, because excessive cell culture time (more than 30 days) negatively impacts nuclear transfer efficiency (Lai et al., Cloning and Stem Cells 5(4):233-241, 2003). Following fibroblast harvest from day 35 fetuses, the cells were frozen within 48 hours. The use of an AAV vector to deliver the gene targeting construct allowed targeting to begin 24 hours after thawing cells and required no cell detachment and re-attachment, which is required in other methods. Multiple cell detachment and re-attachment events (trypsinization) are thought to decrease the ability of a cell to serve as a nuclear donor in nuclear transfer. Further, G418 selection in 48 96-well plates prevents the need for the more conventional, time-consuming isolation of resistant clones with cloning rings. The screen for gene targeted clones was designed such that all positive clones could be identified and frozen within a 3-5 day period. All clones were frozen by day 18, therefore the cells have been in culture approximately 20 days since being harvested from the fetus. In this aspect of the invention, reduction of the time in culture increases the likelihood that cells used as nuclear donors are viable, normal, and euploid.

Accordingly, the invention provides a method of gene-targeting cells, such as pig cells (e.g. pig fetal fibroblasts), in which the number of days in culture (during which targeting and selection takes place) is preferably less than 30 days, preferably 25-29 days, preferably 20-24 days, and more preferably 19, 18, 17, 16, 15, or fewer days. To facilitate this method, the selection can take place in multi-well plates, as described further below. Further, the cells may be frozen shortly after harvest (for example, within 24, 48 or 96 hours). After cell thawing (or after harvest, if the cells are not previously frozen), gene targeting with an AAV vector can be carried out within, for example, 12, 24, 36 or 48 hours, without the use of multiple detachment/re-attachment events, and selection can proceed in an expedited manner, such as by use of multi-well plates (e.g., 96 well plates), prior to freezing.

Other types of vectors, or more specifically other types of targeting construct delivery methods, are also available to those of skill in the art and may be used in the present invention. Such methods include cell transfection methods, including calcium phosphate, lipofection, electroporation, and nuclear injection, all of which can be used to deliver the targeting construct. If the gene is transcriptionally active in the cell being used, then a promoterless selectable strategy can be employed, so that antibiotic resistance will only be found in cells that have had a recombination event within the transcribed unit.

Genetically targeted cells are typically identified using a selectable marker, such as neomycin. If a cell already contains a selectable marker, however, a new targeting construct containing a different selectable marker can be used. Alternatively, if the same selectable marker is employed, cells can be selected in the second targeting round by raising the drug concentration (for example, by doubling the drug concentration), as is known in the art. As is noted above, targeting constructs can include selectable markers flanked by sites facilitating excision of the marker sequences. In one example, constructs can include loxP sites to facilitate the efficient deletion of the marker using the cre/lox system. Use of such systems is well known in the art, and a specific example of use of this system is provided below, in the experimental examples.

Upon obtaining cells in which a target gene (e.g., a LDLR gene) has been targeted (one or both alleles, as described above), nuclear transfer can be carried out. Optionally, the genetically modified nuclear donor cells can be frozen prior to nuclear transfer. Recipient cells that can be used in the invention are typically oocytes, fertilized zygotes, or two-cell embryos, all of which may or may not have been enucleated. Typically, the donor and the recipient cells are derived from the same species. However, it is possible to obtain development from embryos reconstructed using donor and recipient cells from different species.

Recipient oocytes can be obtained using methods that are known in the art or can be purchased from commercial sources. As is known in the art, the donor nucleus or the donor cell itself can be injected into the recipient cell or injected into the perivitelline space, adjacent to the oocyte membrane. The nuclear transfer complex formed in this manner can be activated by standard methods, which may involve electrical fusion/activation or electrical fusion/chemical activation, as is described further below. Further processing of the nuclear transfer complex, including implementation of the complexes into surrogate mothers, is described further below.

The transgenic animals of the invention can be used in the identification and characterization of drug and other treatment methods for the disease or condition associated with mutation of the gene targeted according to the invention. In these methods, for example, a candidate therapeutic agent can be administered to an animal and the impact of the agent on a feature of the disease exhibited by the animal can be monitored. Optionally, the methods can also involve exposure of the animals to environmental or other conditions known to contribute to or exacerbate the disease or condition. For example, in the case of hypercholesterolemia or atherosclerosis animal models having impaired function in the LDLR gene, the effect of the drug on such function can be assessed by measuring the cholesterol-lowering (both total and LDL cholesterol) effect and the impact on progression (or reversal) of hypercholesterolemia or atherosclerosis.

Conversely, the disease status could be exacerbated by feeding the animals a diet high in saturated fat and cholesterol.

With the porcine model of the invention, it is possible to test hypotheses that lead to new treatments, diagnostics, imaging technologies and medical devices, and to evaluate potential therapies for hypercholesterolemia and cardiovascular disease. Likely activities involving the present invention may include evaluating current and future therapeutics for toxicity, pharmacokinetics and efficacy within the same animal. Medical devices makers may study the efficacy of stents (and other medical devices and products) in a relevant, diseased setting. And in the context of medical instruments, noninvasive ultrasound imaging may be evaluated to diagnose and chart the progression of hypercholesterolemia and atherosclerosis.

Availability of animal models for hypercholesterolemia and atherosclerosis allows new investigations and tests of therapeutics in the liver, heart, blood vessels and other organs and affected primarily or secondarily by hypercholesterolemia or atherosclerosis. The screening methods of the invention can be carried out to test the efficacy of new compounds, combinations of new and old compounds, diagnostics, non-pharmaceutical treatments, medical devices, and combinations of the foregoing.

The following Examples are meant to illustrate the invention and are not meant to limit the scope of the invention in any way.

EXAMPLES

Pigs with a null allele in their LDLR gene provide a valuable tool for assessing the porcine atherosclerosis and hypercholesterolemia phenotypes. In one embodiment, the pigs of the present invention will have the coding sequence of one allele of the pig LDLR gene has disrupted by a neomycin resistance cassette and a translation termination codon. In another embodiment, the disruption of both alleles in a pig is achieved by conventional breeding, as noted above, as well as by further gene targeting methods. The pigs of the present invention can be used to develop and test therapeutics to treat atherosclerosis and hypercholesterolemia. Further, the pigs of the present invention can also be used to understand the pathogenesis of cardiovascular disease, both in the animal and in tissues from the animal.

Example 1: LDLR Targeting Construct

The pig genome project is nearing completion, however a fully annotated genome is not yet available. While many porcine cDNA (or coding) sequences and some large spans of genomic sequence can be found in public databases, only the porcine LDLR cDNA sequence is available at this time (SEQ ID NO. 1). By comparing the porcine LDLR coding sequence with the human LDLR gene, the intron-exon boundaries for porcine exons 1-18 were determined. Exon 4 of porcine LDLR was selected as a target for disruption and the intron-exon boundary sequence information was used to design primers to amplify a Yucatan miniature pig genomic clone spanning exon 2 to exon 6. This resulted in a PCR product of ~9 kb in length. DNA sequence analysis revealed this PCR product to contain porcine LDLR exons 3, 4, and 5 and an intervening intron sequence (SEQ ID NO. 2). Multiple, independent clones were sequenced in order to determine a consensus. This sequence (SEQ ID NO: 2) was used as a template to generate the 5' and 3' homology arms of the gene-targeting vector (SEQ ID NO. 3).

Figure 2:
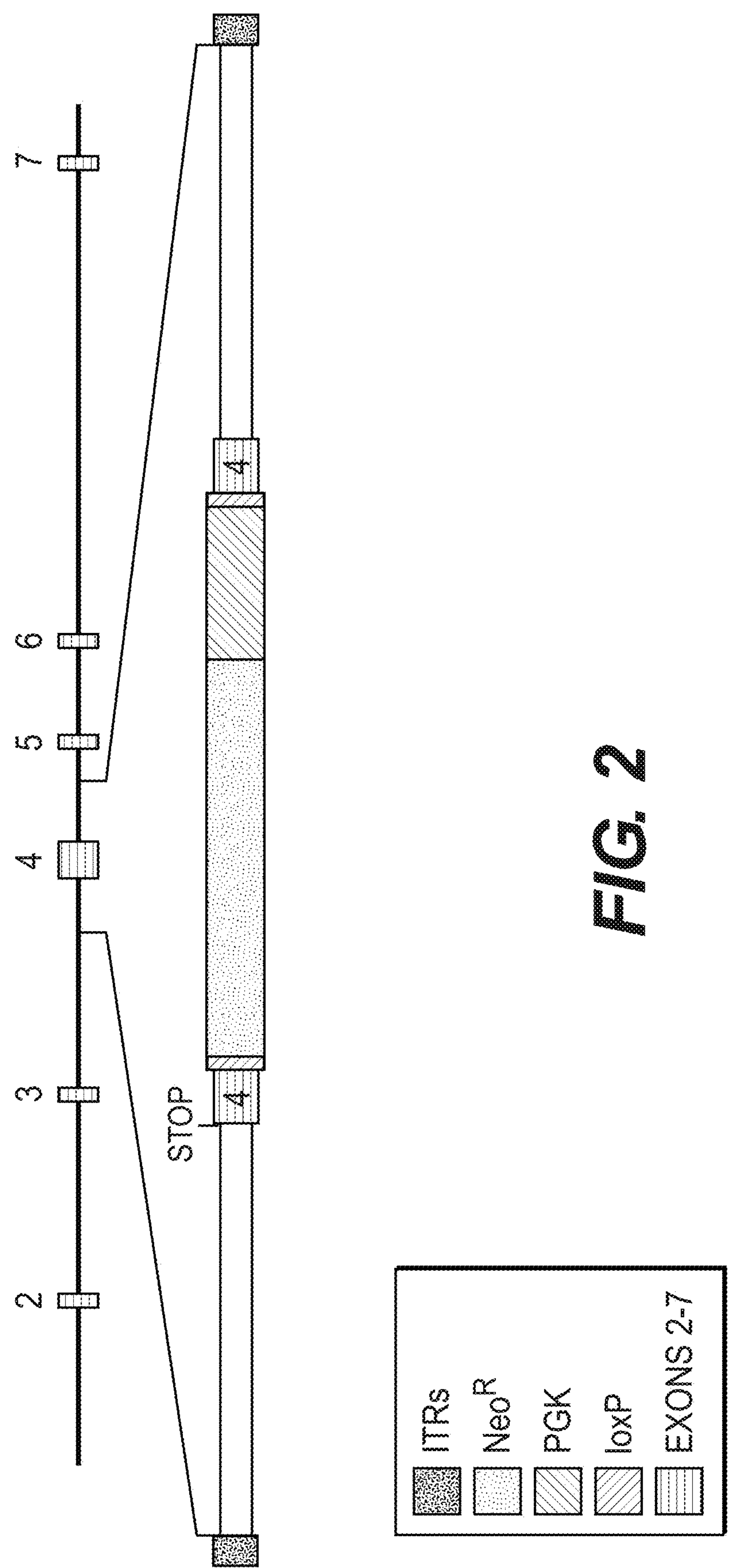
FIG. 2 is a schematic drawing of the gene targeting vector (SEQ. ID. NO: 3) used to disrupt porcine LDLR. Exons 2-7 of porcine LDLR are depicted in boxes. $Neo^R$ contains a neomycin resistance cDNA driven by the phosphoglycerate kinase (PGK) promoter and flanked by loxP sites. The rAAV inverted terminal repeats (ITRs) are also shown. Each homology arm is about 1.4 kb in length.

Homologous recombination was used to disrupt the endogenous porcine LDLR gene. To accomplish this, a neomycin-resistance cassette ($Neo^R$) was inserted into exon 4 of porcine LDLR (FIG. 2) (SEQ ID NO: 3). Exon 4 encodes a necessary portion of the ligand-binding domain. Importantly, this exon was targeted in the murine LDLR knockout animals, and LDLR function was successfully abolished. Ishibashi, S et al., J Clin Invest 92 (2), 883-93, 1993. A premature termination codon was also engineered immediately upstream of the $Neo^R$ insertion. This strategy was adopted to maximize the likelihood of a non-functional LDL receptor.

A plasmid carrying the LDLR targeting vector was generated using standard molecular biology techniques known to those of skill in the art. Proper sequence was confirmed by DNA sequence analysis. The plasmid was then submitted to the University of Iowa Gene Transfer Vector Core for production of recombinant adeno-associated virus (rAAV). rAAV was chosen because it has been used to efficiently deliver gene targeting vectors to cell lines and primary cells. Russell, D. W et al., Nat Genet 18 (4), 325-30, 1998. Further, rAAV has been previously used to introduce two different targeted modifications to the porcine CFTR gene. Rogers, C. S et al., J Clin Invest 118 (4), 1571-7, 2008. Using a rAAV vector has several advantages in that it delivers single-stranded DNA to the nucleus, the amount of DNA per cell is small, and it can infect many cell types. Importantly, the ratio of homologous recombination events to random integrations is more favorable than that seen with electroporation of lipid-mediated transfection. Vasquez, K. M et al., Proc Natl Acad Sci USA 98 (15), 8403-10, 2001.

Example 2: Targeting LDLR in Porcine Fetal Fibroblasts

Approximately $1.5\times10^6$ Yucatan miniature pig fetal fibroblasts—both male and female—were infected with rAAV1 (MOI≅100-800K) carrying the LDLR targeting vector. After 24 hours, cells were transferred to a series of 96-well plates and G418 (100 μg/ml) was added to the media for selection of targeted cells. Fourteen days later, surviving cells were observed in 20-40% of wells, and each well of the 96-well plates were "replicated" by splitting among three plates: 1) 96-well culture plates for cell expansion, 2) 96-well culture plates for potential cryopreservation, and 3) 96-well PCR plates for cell lysis.

Figure 3A:
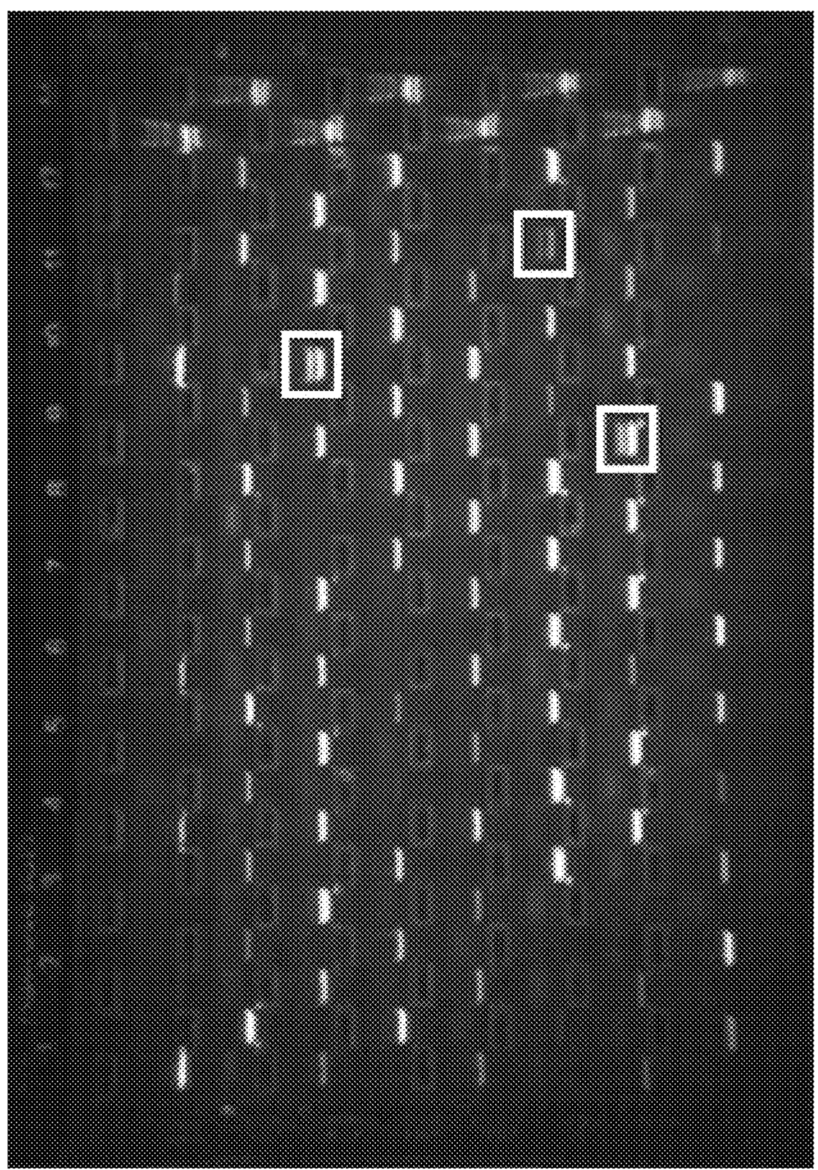
FIG. 3A shows a representative 96-well gel containing 3 PCR-positive clones (boxed). The other wells represent $NEO^R$ clones resulting from random integration, or in the case of lighter bands, leftover DNA from dead cells. Each PCR-positive clone was re-electrophoresed on a conventional agarose gel to confirm proper size as shown in FIG. 3B. Expected sizes were 1.8 kb for wild-type LDLR and 3.5 kb for targeted LDLR. Lanes 1-6 represent LDLR-targeted cells and lane 7 represents wild-type cells.

Cell lysates were screened by PCR to identify wells containing gene-targeted clones and any PCR-positive clones were frozen. This assay exploited the size difference caused by the insertion of the ~1.7 kb $Neo^R$ (FIG. 3A, B). PCR identified 33 LDLR+/− male cell lines and 83 LDLR+/− female cell lines.

By the time LDLR-targeted cells were frozen, they had been in culture only 15-17 days. This short time frame is important as the longer cells are in culture, the less efficient they are as nuclear donors. Positive clones were also passaged from the "cell expansion" plates to provide genomic DNA for downstream applications. Because many of the cell lines began to senesce before large quantities of genomic DNA could be obtained, whole-genome amplification (REPLI-g, Qiagen) was used to provide DNA for Southern blot analysis.

Southern blots with LDLR− and $Neo^R$-specific probes were used to identify clones with a targeted LDLR allele and that were free of random integration. Furthermore, DNA sequence analysis was used to confirm the proper targeting site (FIG. 3C). Seven LDLR+/− male and five LDLR+/− female cell lines were identified that meet the above criteria—processing all of the PCR-positive cell lines is not necessary, however those cells and DNA were preserved, if needed.

Example 3: Nuclear Transfer

LDLR+/− male and female cells were used for somatic cell nuclear transfer (SCNT) to produce live male and female offspring. Specifically, in vitro matured pig oocytes were obtained from a commercial supplier. After 42 to 44 hr of maturation, oocytes were freed of cumulus and corona cells by vigorous pipetting. Metaphase II oocytes with an intact plasma membrane were selected and enucleated. To do this, the meiotic metaphase II chromosomes were stained by Hoechst dye and visualized. A transfer pipette was inserted through the zona pellucida and the chromosomes aspirated into the pipette and the pipette removed.

LDLR+/− fetal fibroblasts were thawed and selected according to their size and shape (small cells with smooth membrane). Selection of small cells increases the probability that cells from these mixed populations will be in G1 or G0, as cells in G2 would be expected to be larger. A single cell was then transferred into the perivitelline space with the same pipette used for enucleation. Care was taken to ensure contact between the plasma membrane of the cytoplast and the donor cell. Reconstructed embryos were fused and simultaneously activated. Cytoplast-fibroblast complexes were placed between 2 electrodes (1 mm apart) overlaid with fusion medium and aligned manually. Following electrical fusion and activation, the nuclear transfer embryos were placed in vials containing standard incubation media and transferred to an Exemplar Genetics facility in a shipping incubator maintained at 38.5° C. The SCNT process is described in U.S. Pat. No. 7,989,675.

Example 4: Surrogate Preparation and Embryo Transfer

Gilts exhibiting their second or greater post-pubertal estrus were used as embryo recipients. Gilts that have exhibited estrus the day of the nuclear transfer or the day after were anesthetized. A small abdominal incision exposed the ovaries and oviducts. One hundred to one hundred fifty nuclear transfer embryos were loaded in a catheter and injected into the oviduct of the recipient. Pregnancy status of the surrogates was monitored via ultrasound. The transfer of such a large number of embryos at one time is necessary since it is generally accepted that a minimum of 4 conceptuses are required to initiate a pregnancy, and only a small percentage of the nuclear transfer embryos develop. In some cases, a recipient that maintains a pregnancy to full term does not initiate parturition or mammogenesis. In those cases, a caesarean section is performed and the piglets fed by hand.

Figures 4A, 4B:
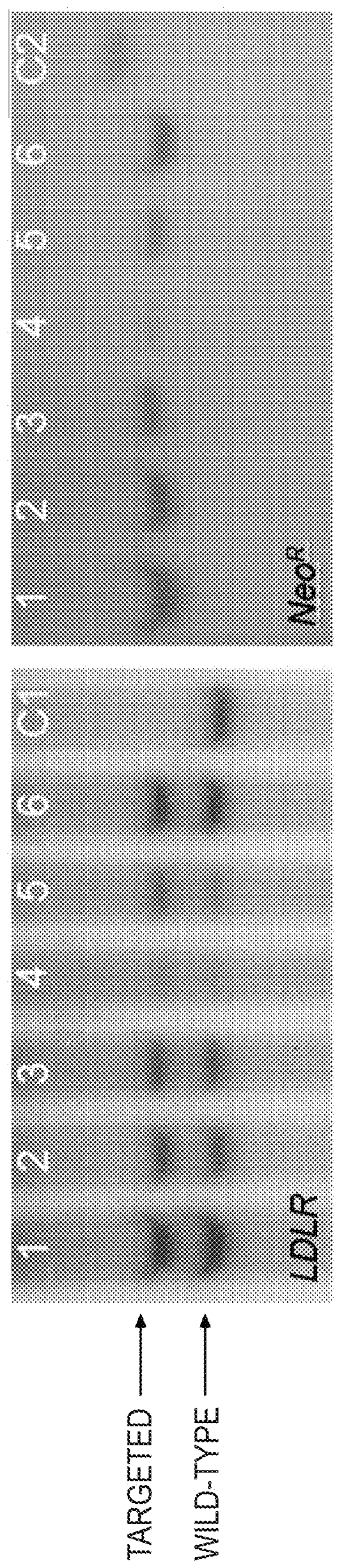
FIG. 4A shows Xmnl-digested genomic DNA that was hybridized with a probe that detects porcine LDLR downstream of the targeting vector boundary. The LDLR-targeted allele produced an approximately 7.8 kb band, and the wild-type band is approximately 6.0 kb.
In FIG. 4B, the same DNA was hybridized with a probe that detects the $Neo^R$ cassette, yielding only the targeted 7.8 kb band. Lanes 1-6 contain DNA from individual cloned fetuses. Lane C1 contains XmnI-digested DNA from a wild-type pig, and lane C2 contains BglII-digested DNA from a CFTR+/− pig ($Neo^R$-positive).

Two pregnancies were terminated early in order to isolate LDLR+/− fetuses for the purpose of making LDLR+/− fetal fibroblasts. FIG. 4 shows a Southern blot of genomic DNA from LDLR− targeted pig fetuses (gestational day 35). In FIG. 4A, XmnI digested genomic DNA was hybridized with a probe that detects porcine LDLR downstream of the targeting vector boundary. The LDLR-targeted allele produced an approximately 7.8 kb band, and the wild-type band is approximately 6.0 kb. In FIG. 4B, the same DNA was hybridized with a probe that detects the $Neo^R$ cassette, yielding only the targeted 7.8 kb band. Lanes 1-6 contain DNA from individual cloned fetuses. Lane C1 contains XmnI-digested DNA from a wild-type pig, and lane C2 contains BglII-digested DNA from a CFTR+/− pig ($Neo^R$-positive).

All other pregnancies were allowed to go to full term. In total, 24 LDLR+/− males and 33 LDLR+/− females were created. A summary of LDLR gene targeting and SCNT activity is shown in Table 1 (FIG. 7).

Figures 5A, 5B:
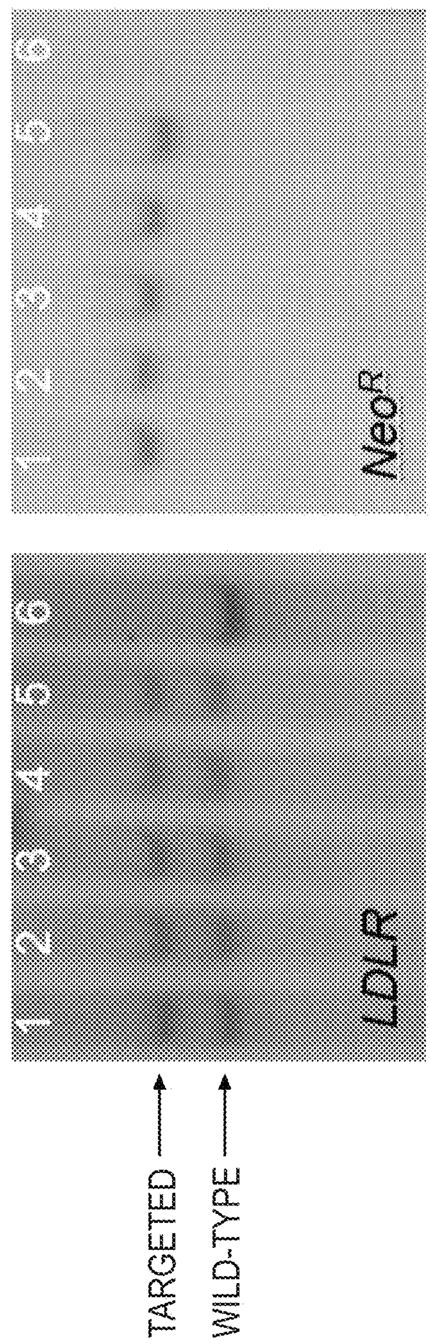
FIG. 5A shows Xmnl-digested genomic DNA that was hybridized with a probe that detects porcine LDLR downstream of the targeting vector boundary. The LDLR-targeted allele produced an approximately 7.8 kb band, and the wild-type band is approximately 6.0 kb.
In FIG. 5B, the same DNA was hybridized with a probe that detects the $Neo^R$ cassette, yielding only the targeted 7.8 kb band. Lanes 1-5 contain DNA from individual LDLR+/− piglets, and lane 6 contains DNA from a wild-type pig.

Genomic Southern blots (FIG. 5) confirm the LDLR+/− genotype as well as the presence of a single NeoR cassette (no random integration was detected), and DNA sequencing confirmed the intended gene disruption.

Figure 6:
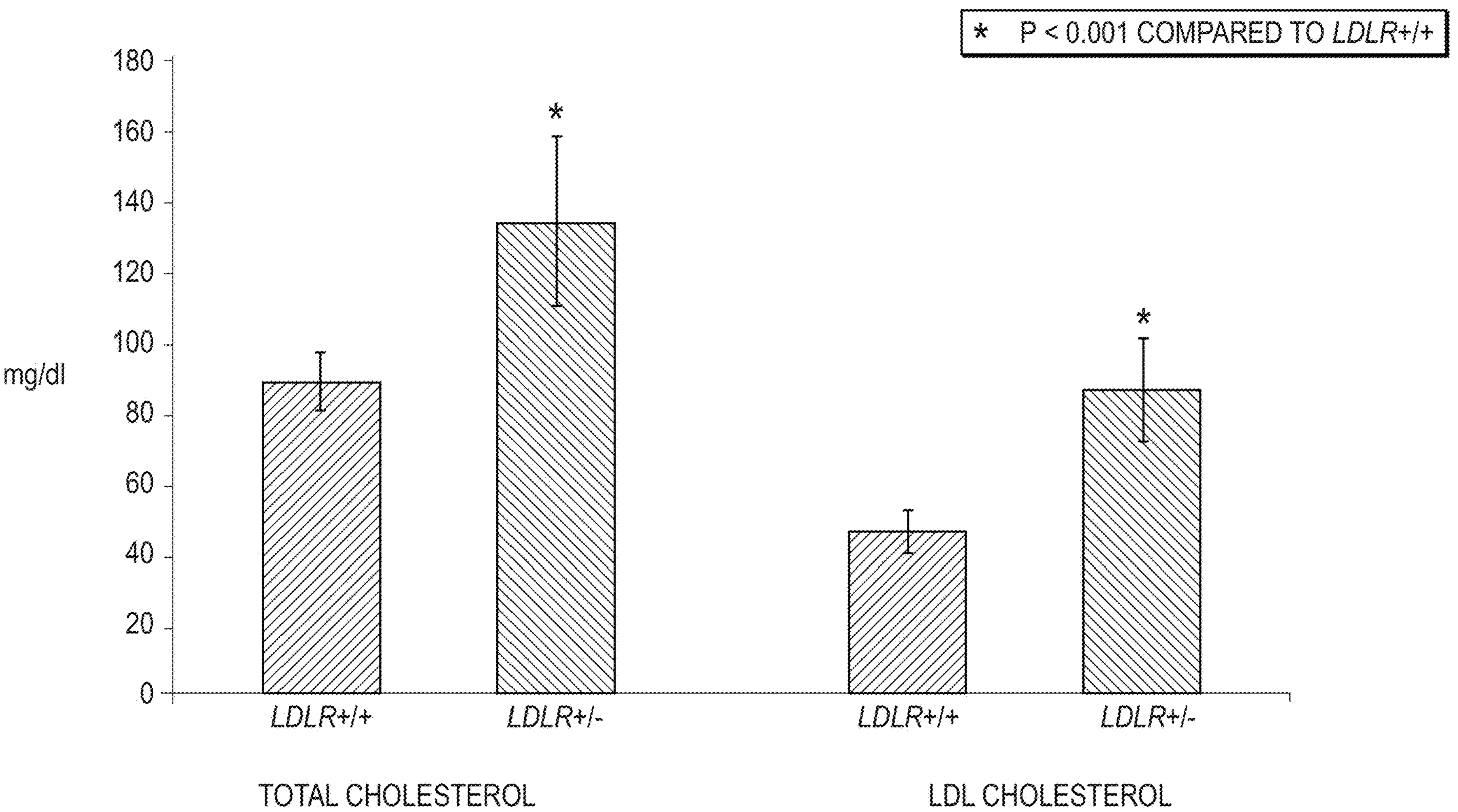
FIG. 6 shows a preliminary assessment of plasma cholesterol levels (P) in LDLR-targeted pigs. Total plasma cholesterol and LDL cholesterol were measured in 8-week old LDLR+/− (number=17) and LDLR+/+ (number=5) intact males. Asterisks indicate P<0.001 compared to LDLR+/+. Error bars represent standard deviation (SD).

As a preliminary assessment of phenotype in 8-week old LDLR+/− male animals, total cholesterol and LDL cholesterol from plasma were measured. FIG. 6 demonstrates there is a significant difference between LDLR+/− animals and wild-type animals.

Example 5: Breeding to Produce LDLR−/− Pigs

Three LDLR+/− males and 24 LDLR+/− females were retained for breeding purposes. To date, 16 litters have been produced yielding the expected Mendelian inheritance of 20 LDLR+/+, 40 LDLR+/−, and 21 LDLR−/− pigs. Since the sires and dams were each derived via SCNT from single, LDLR-targeted cell lines, each litter produced from this mating can be considered to be from the same cross.

Example 6: Lipid Chemistry Analysis

Figure 9:
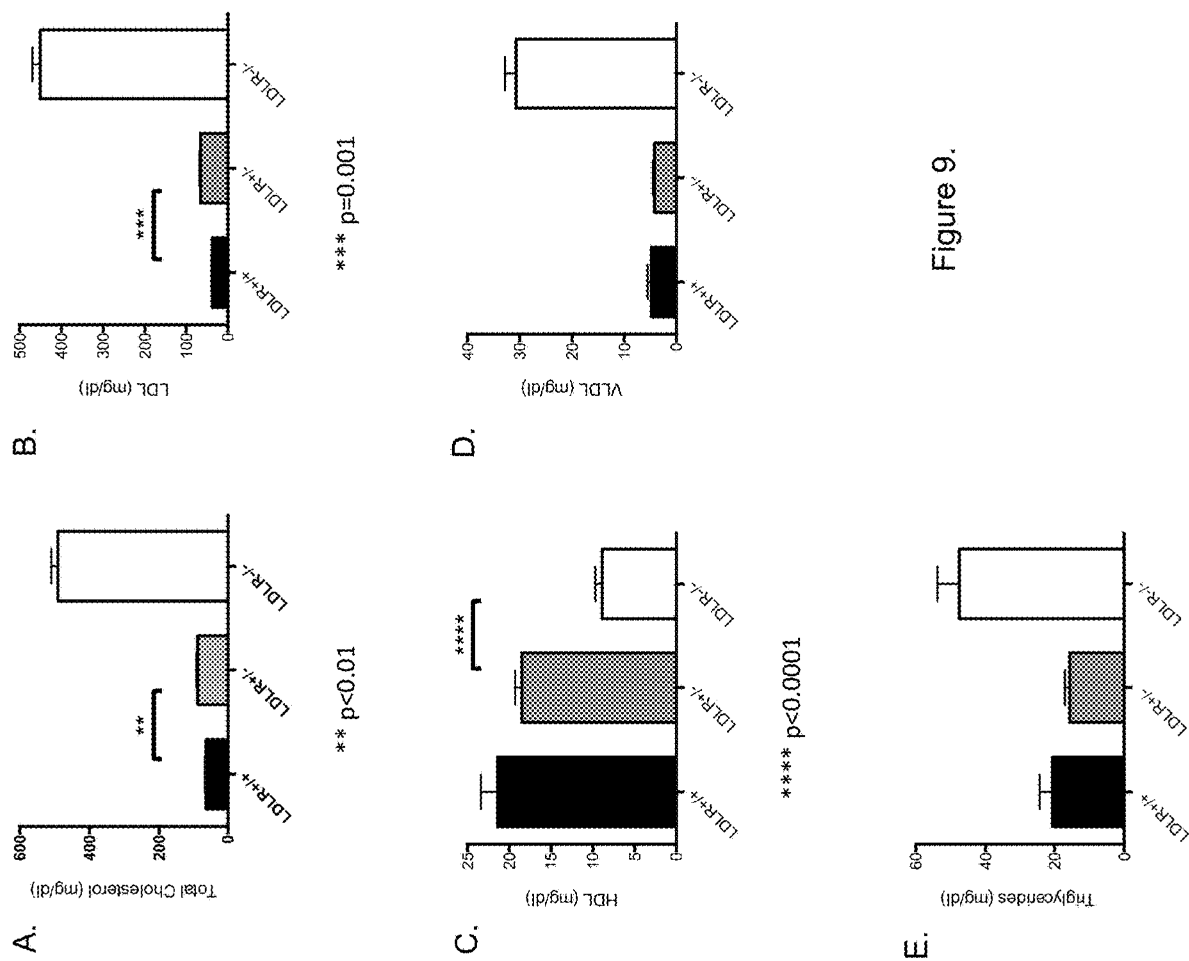
FIG. 9 shows blood lipid analysis in newborn LDLR+/+, LDLR+/−, and LDLR−/− piglets. Plasma was obtained from blood drawn from piglets at the time of birth and before any animals had suckled.

Plasma cholesterol levels were measured in LDLR+/+, LDLR+/−, and LDLR−/− piglets immediately at birth before piglets could suckle. This allows an initial assessment before lipid levels are affected by the sow's cholesterol- and fat-rich colostrum and milk. Total cholesterol was higher in LDLR-targeted pigs than in their LDLR+/+ littermates (FIG. 9). LDLR+/− piglets exhibited a slight, but statistically significant elevation in total, LDL, and VLDL cholesterol, while LDLR−/− pigs had dramatically elevated levels for each. HDL was decreased in LDLR−/− pigs, though not in LDLR+/− pigs. Finally, homozygous animals also had a significant elevation in triglycerides.

Figure 10:
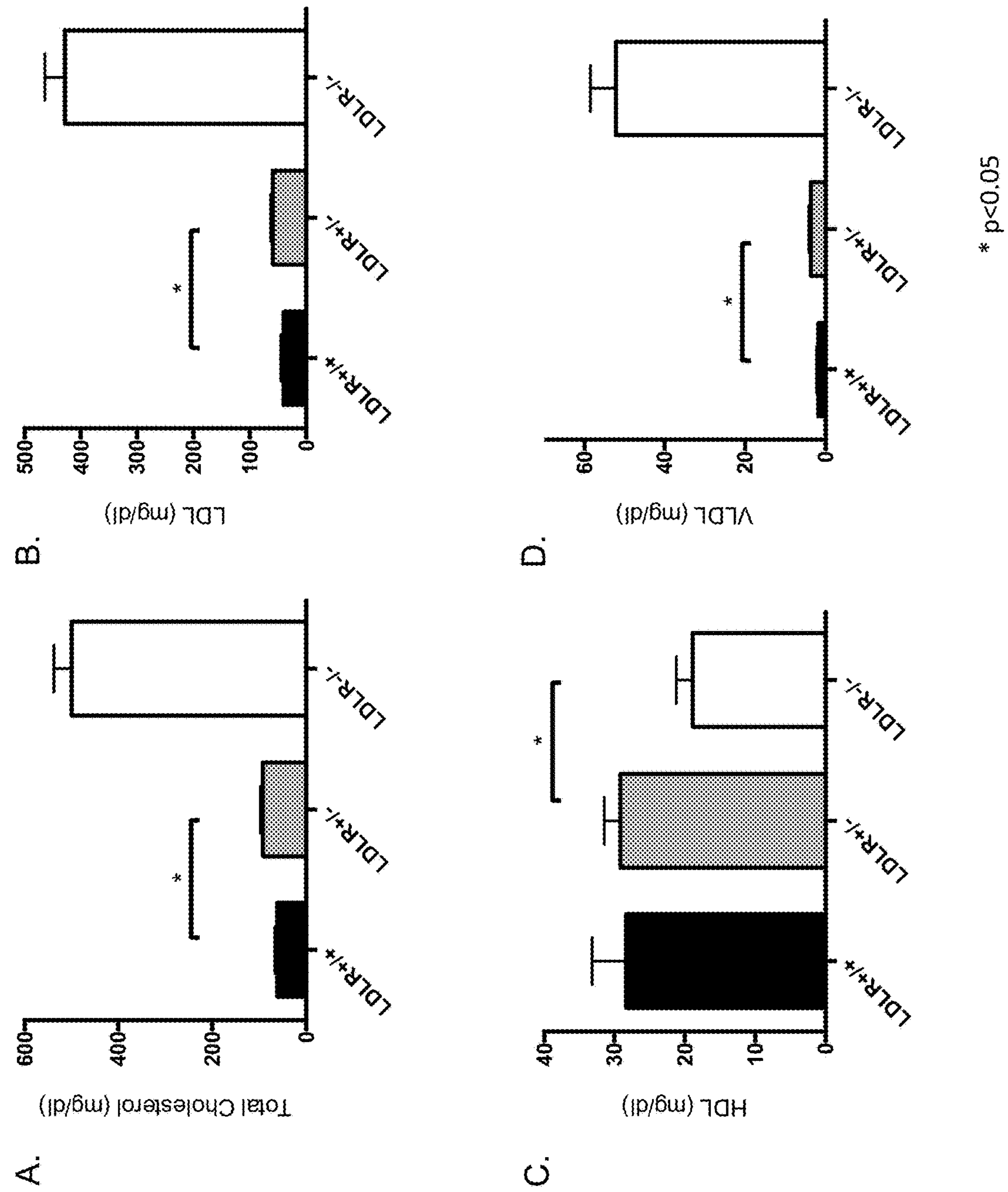
FIG. 10 shows blood lipid analysis in 12-week old LDLR+/+, LDLR+/−, and LDLR−/− pigs. Plasma was obtained from blood drawn from pigs at 12 weeks of age.

Cholesterol levels in pigs can vary widely while nursing (data not shown). At 3-4 weeks of age, pigs were weaned and placed on a standard diet consisting of zero cholesterol and 3% fat. By 12 weeks of age (~8-9 weeks post-weaning) cholesterol levels stabilized at levels similar to what was seen pre-suckle (FIG. 10).

Example 7: Early Atherosclerosis in a LDLR−/− Pig

Figure 11:
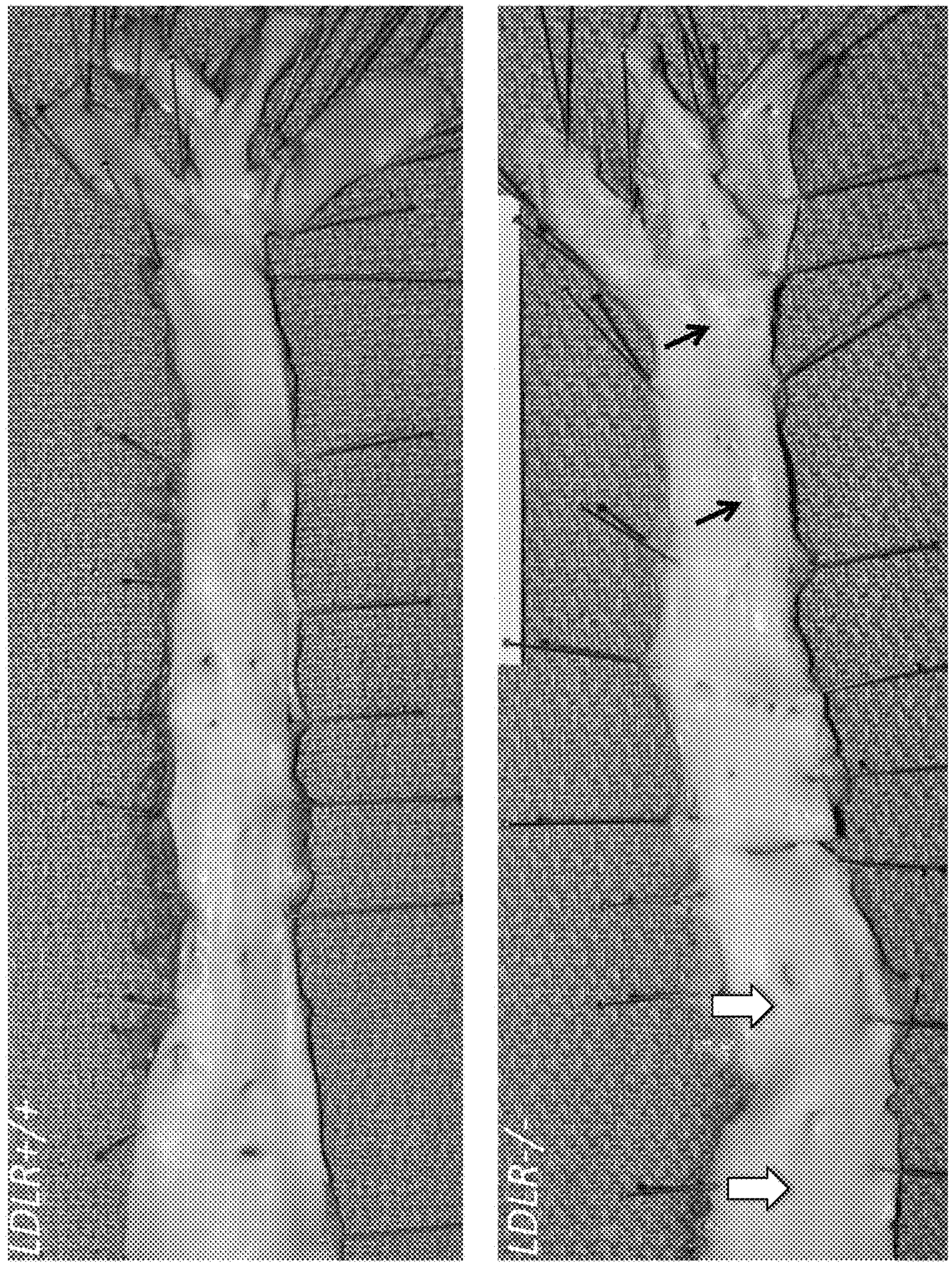
FIG. 11 shows abdominal aortas from 7-month old LDLR+/+ and LDLR−/− pigs. Abdominal aortas were harvested from 7-month old LDLR+/+ (upper) and LDLR−/− (lower) littermates that were fed a standard pig diet (no cholesterol, 3% fat). The LDLR+/+ pig shows no signs of atherosclerosis. However, the LDLR−/− pigs show extensive atherosclerosis. Black arrows indicate some (but not all) raised atherosclerotic lesions. There are also uniform lipid-rich regions of atherosclerosis on the surface of the tissue in the LDLR−/− pig indicated by white arrows.

To determine whether a LDLR−/− pig would show the presence of atherosclerosis having been raised on a standard diet (no cholesterol, low-fat), one LDLR−/− female and a LDLR+/+ littermate control were necropsied at 7 months of age and the presence of atherosclerosis was assessed in the abdominal aorta. In FIG. 11, atherosclerotic lesions are clearly shown in the abdominal aorta of the LDLR−/− pig, while the LDLR+/+ abdominal aorta is completely free of lesions. FIG. 11 also shows raised lesions as well as uniform lipid-rich regions throughout.

Example 8: Confirmation of Genotype

Figure 12:
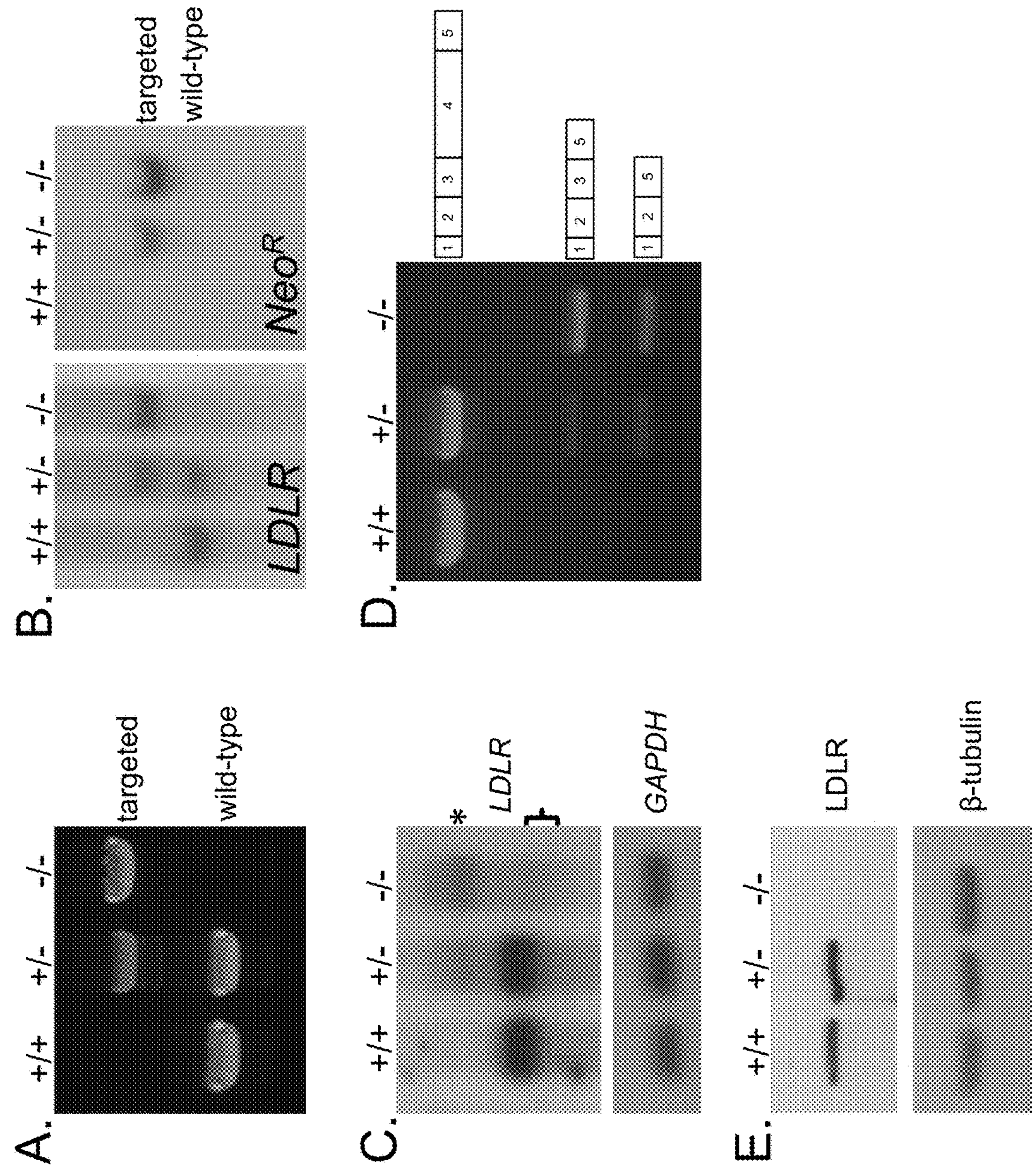
FIG. 12 shows the molecular and biochemical characterization of LDLR+/+, LDLR+/−, and LDLR−/− pigs.

FIGS. 12A and 12B shows representative LDLR+/+, LDLR+/−, and LDLR−/− genotyping results via PCR and Southern blot. As discussed above, exon 4 was disrupted with a $Neo^R$ cassette and inserted a premature termination codon. The most likely consequence of this mutation is the induction of nonsense-mediated mRNA decay. However, should a protein be translated, it would be truncated in the ligand-binding domain, lack the transmembrane-spanning segment, and be non-functional. An additional possibility could be the skipping of exon 4 via nonsense-associated altered splicing. This, too, would result in a protein with no ability to bind LDL. Northern blot analysis of liver RNA suggests that the targeted allele produces no normal LDLR mRNA (FIG. 12C), however RT-PCR reveals the presence of truncated mRNAs resulting from mRNA lacking exon 4 as well as exons 3 and 4 (FIG. 12D), each scenarios which should result in frameshift mutations. Finally, a western blot of liver extracts shows that LDLR−/− pigs produce no normal LDLR protein (FIG. 12E).

Other Embodiments

All publications, patents, and other citations noted in this specification are incorporated herein by reference as if each individual publication, patent, or other citation were specifically and individually indicated to be incorporated by reference. Although the invention has been described above in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Use in the claims and elsewhere herein of singular forms, such as "a" and "the," does not exclude indication of the corresponding plural form, unless the context indicates to the contrary. Thus, for example, if a claim indicates the presence of "a" mutation in "a" gene, it can be interpreted as covering one or more mutations, in one or more genes, unless otherwise indicated.

Other embodiments are within the following claims.

What is claimed is:

1. A transgenic Yucatan miniature pig whose genome comprises a homozygous inactivation of exon 4 in its endogenous low-density lipoprotein receptor (LDLR) gene, wherein said exon 4 comprises insertion of a gene targeting vector comprising the nucleotide sequence as set forth in SEQ ID NO: 3, wherein said pig produces no functional LDLR protein, and wherein said pig exhibits an increased level of triglycerides, LDL and VLDL cholesterol as compared to a wild type Yucatan miniature pig.

2. A transgenic Yucatan miniature pig whose genome comprises a heterozygous inactivation of exon 4 in its endogenous LDLR gene, wherein said exon 4 comprises insertion of a gene targeting vector comprising the nucleotide sequence as set forth in SEQ ID NO: 3, wherein said pig shows reduced expression of LDLR gene and an increased level of and VLDL cholesterol as compared to a wild type Yucatan miniature pig.

3. A method of making the Yucatan miniature pig of claim 2, the method comprising:

(a) inactivation by inserting a heterologous polynucleotide comprising the nucleic acid sequence of SEQ ID NO:3 into exon 4 of the Yucatan miniature pig LDLR gene via homologous recombination in a Yucatan miniature pig fetal fibroblast;

(b) culturing the fetal fibroblast in a medium that selects for the neomycin-resistance gene for less than 20 days;

(c) introducing the nucleus of the fetal fibroblast into an enucleated Yucatan miniature pig oocyte to form a Yucatan miniature pig embryo; and (d) transferring the Yucatan miniature pig embryo into a recipient female Yucatan miniature pig and allowing the embryo to develop such that a heterozygous transgenic Yucatan miniature pig of claim 2 whose genome comprises a heterozygous disruption of the LDLR gene is obtained.

4. The method of claim 3, wherein the fetal fibroblast is from a male pig.

5. The method of claim 3, wherein the fetal fibroblast is from a female pig.

6. The method of claim 3 further comprising the step of:

(e) breeding the heterozygous transgenic swine obtained in (d) such that a homozygous Yucatan miniature pig of claim 1 is obtained.

7. The method of claim 6, wherein the fetal fibroblast is from a male pig.

8. The method of claim 6, wherein the fetal fibroblast is from a female pig.

* * * * *

SEQUENCE LISTING

```
<160> NUMBER OF SEQ ID NOS: 5

<210> SEQ ID NO 1
<211> LENGTH: 2538
<212> TYPE: DNA
<213> ORGANISM: Sus scrofa

<400> SEQUENCE: 1

atgaagtcca cgggctgggt cctgcgatgg gctgtcgcct tgctcattgc tgcggtggca      60

gctgcagtgg aagagaaatg tgggagaaac gagttccagt gccgagacgg gaaatgcatc     120

tcctacaagt ggatttgtga tgggaacacc gagtgcaagg acgggtccga tgagtccctg     180

gagacgtgca tgtctgtcac ctgcaagata ggggacttta gctgtggggg ccgtgtcaac     240

cgctgcattc ctgagtcttg gaggtgtgac ggtcagcagg actgcgagaa tggctcagat     300

gaggaaggct gttcccccaa gacgtgctcc caagatgagt tccgctgcca ggacggcaag     360

tgcatcgccc caaagtttgt ctgtgactcg gaccgggact gcctggacgg ctcggatgaa     420

gcatcctgcc ccacacccac ctgtggcccc gccagcttcc agtgcaacag ctccacctgc     480

atccctgagc tgtgggcctg tgatggtgat cctgactgcg aggacggctc agacgagtgg     540

ccacagcact gcaggagcca cagctcatca ctccccgaga ggagcaacaa cccctgctca     600

gccctcgagt tccactgcca cagtggcgag tgcatccact ccagctggcg ctgcgacgga     660

gacactgact gcaaggacaa gtctgacgag gagaactgcg atgtggccac gtgccggcct     720

gacgagttcc agtgctcaga cgggacctgc atccatggta gccggcagtg cgacagggaa     780

tatgactgca aggacatgag cgacgagcag ggctgtgtca atgcgactct gtgcgagggg     840

cccaacaagt tcaagtgtca aagcggcgag tgcatctcct tggacaaagt gtgcaactca     900

gtcagggact gccgggactg gtcagacgag cccctcaagg agtgtgggac caacgagtgt     960

ctggacaaca agggtggctg ctcccatatc tgcaatgacc tcaagatcgg ctatgagtgc    1020

ctctgtcccg agggcttcca gctggtggat aagcacagat gcgaagatat cgacgagtgt    1080

caggacccag acgcctgcag ccagatctgc gtgaacctcg agggcagcta caagtgccag    1140

tgtgaggagg gcttccagct ggagcctctc accaaggcct gcaaggccat aggcaccatc    1200

gcctacctct tcttcaccaa ccgccacgag gtgaggaaga tgaccctgga ccgtagtgag    1260

tacaccagcc tcatccccaa cctgaagaac gtggtcgctc tggacactga ggtggccagc    1320

aatagaatct actggtctga cctgtctcag aggaagatct acagtaccca gatcgacagg    1380
```

-continued

```
gcccccagct tttcctccta tgacaccatt attggcgaag atctccaggc ccccgatggg   1440

ctggcggtgg actggatcca cagcaacata tactggactg actccatcct gggcactgtc   1500

tccgtggctg acaccaaggg cgtgaagagg aagactctct tccaagagaa aggctccaag   1560

ccacgggcca ttgtggtgga ccctgtccat ggcttcatgt actggactga ttggggaacc   1620

cccgccaaga tcaagaaggg cggcctgaac ggagtggacg tctactcgct ggtgacggag   1680

gacatccagt ggcccaatgg catcaccctg gatctttctg gcggccgcct ttactgggtc   1740

gactccaagc tccactccat ctccagcatc gatgtcaacg gggggaaccg gaagaccgtc   1800

ctggaggaca agacgaagct ggcgcacccc ttctccttgg ccatttttga ggataaagta   1860

ttttggacag atataatcaa cgaagccatt ttcagtgcca accgcctcac aggctcggac   1920

atacatttga tggcagaaaa cctgttgtct ccagaggaca ttgtcctttt ccacaacctc   1980

acacagccga gaggggtgaa ctggtgtgaa aggaccgccc tccaaaacgg tggctgccag   2040

tacctgtgtc tgccagctcc acagatcaac ccacgctcgc cgaagttcac ctgtgcctgc   2100

ccggatggca tgctgttggc caaggacatg aggagctgtc tcacagagac tgaacctgca   2160

ggaaccaccc agggaccttc catggtcaac tcgacagctg tggggccaaa gcacaccgcc   2220

agctctgagc tcaccacagc cgagtcagtg acgatgtccc aacatgccct gggcgacgtt   2280

gctggccgag gagtcactga gaagccccag agcgtgggtg ctctgtacat tgtcctcccc   2340

attgcactgc tcatcctcct cttcttcgga accttcctcc tctggaagaa ctggaggctt   2400

aagagcatca acagcattaa cttcgacaac cctgtgtacc agaagaccac ggaagacgag   2460

gtccacatct gccgcagcca ggacggctac acctacccct cgagacagat ggtcagcttg   2520

gaggatgacg tggcgtga                                                 2538
```

```
<210> SEQ ID NO 2
<211> LENGTH: 8483
<212> TYPE: DNA
<213> ORGANISM: Sus scrofa

<400> SEQUENCE: 2

gtccctggag acgtgcagtg agtccccttg ggttgtgacc tttctgacca tggtgggtga     60

tagactcggt gggaatcagc ttgtgtattg atgcattctg ctgtgaatta ggatgtgggc    120

ggagaaggta tttctggaac tttcctttaa tggccctccc gttttttttt taatgagatg    180

aaataggatt ttttttttt ttttttttt tggtattttt acctcatatg gaggttccca    240

ggctaggggt ctaaccggag ctgtagccag atctgagctt cgtctgtgac ctataccaca    300

gctcatggca acgctggacc cttaacccac tgagcaaggc cagggatcga acctgggtcc    360

tcatggatgc ttgttgggtt cgtttccact gagccacaac tggaactcct agattctttt    420

ctagtatagt tattacaaga tattgaatat agtttcctgt gctatgcagt aggtccttgc    480

cgtctatcta tttaatatgt agtgtcgtgt atctgttaat tccaaactcc taatttatcc    540

ctatagccct taccaactgg tcacttaatt tttttccaat ttaatataat ttttatttta    600

ttttagtctt tttgcctttt cttgagtgct cctgtggcat atggaggttc ccaggctagg    660

ggtctaatcg gagctgtagc cactggccta cgccagagcc acagcaaggc aggatctgag    720

ccgtgtctgt gacctacacc acaactcaca gcaacaccag atccttaacc cactgagcaa    780

ggccagggat cgaacccgca acctcatggt tcctagtcag attcgttaac cactgagcca    840

ccatgggaac tcctataatt tttattttat taaataaaat gtaaagggga gctcgctact    900

cacttttggc tgctcccaca gcatgcagaa gttcccaggc cagcgatgga accctagcca    960
```

-continued

```
cagcagtgac aatgccagat ccttaaccat taggccacca gggaactcca aggtttttc   1020
ctttgcaaag cccagactgg caaggcaggt tggtcttcct atgagttaag ggtcaatgct   1080
gttttctccc acagtgtctg tcacctgcaa gataggggac tttagctgtg gggccgtgt   1140
caaccgctgc attcctgagt cttggaggtg tgacggtcag caggactgcg agaatggctc   1200
agatgaggaa ggctgttgta agtggggtcc ctcacctcgt gggccatggg cctcagccac   1260
gtccaagtga cccgaccaga ttctggtctg aggtcagaat ttgttcctcc agctgagagt   1320
tccacaaaga aacaaggctg atagtttcag atgggaaggc atgtggcagc tggctctttg   1380
attttattca ttatttataa tttccttttc agctatataa actttttttt tttttttgg   1440
ccgcatctat ggcatgtgga aattcctggg ccagggatca aacctgtgcc acagcagtga   1500
caaccctgga tcattaaccc actgagccac tggggaactc ttgtatagac atgtctttca   1560
tgaagtgagg ctctttaaaa aaacaaaaac ctctggacag gttgtaataa cctataatgg   1620
gagagaatgt aaaaggaaga gaaatatata tatttctctc tctctttttt ttatttggtc   1680
gcatccactg catatcaagt tcccaggcca gggactgaat tcaaggtgca gctgcaaccc   1740
actgcacagc agtgacaact gccagatcct taacctgctg aacgaccagg gaactccctc   1800
tttttcatgt tcttttccat tatagtttat tacaagaaat tgaatgtgga tccctgtgca   1860
aactcttaaa tagtgcttcc catgtgccca gcccaacctg ggaactttac acacgttcct   1920
cacagtaaca ccttgagaca cgaacagacg tccgaggcat tgagagggcc gggagctggg   1980
tgggtatctg ggtggggcag tggttccaaa tccagggccc ctgactacta ccccaggtcc   2040
actcactggg cttggcctgt cctgggctca gtgtccccat ctatgcagtg ggctggtgta   2100
gggcctcccc ggtaacctgg ctgtgatctt ctgtctattt ctgaagcccc caagacgtgc   2160
tcccaagatg agttccgctg ccaggacggc aagtgcatcg ccccaaagtt tgtctgtgac   2220
tcggaccggg actgcctgga cggctcggat gaagcatcct gccccacacc cacctgtggc   2280
cccgccagct tccagtgcaa cagctccacc tgcatccctg agctgtgggc ctgtgatggt   2340
gatcctgact gcgaggacgg ctcagacgag tggccacagc actgcaggag ccacagctca   2400
tcactccccg agaggagcaa caacccctgc tcagccctcg agttccactg ccacagtggc   2460
gagtgcatcc actccagctg gcgctgcgac ggagacactg actacaagga caagtctgac   2520
gaggagaact gcggtagggg cgccttgggg atcccttcac ctgtccctgg gccctcctgt   2580
gtgggggtg gggggctggc cagtgccttt aggtggttct gatcttggag agacagctgt   2640
gagtgatggc tcgaagcaag atcttaattc tctgctcggg aatcaaacct gggcagcctg   2700
ggtgttccgt ggtggctcag tggttaacga atctgactag gaaccatgag gttgcaggtt   2760
cgatccctgg ccttgctcag tgggttaagg atctggtgtt gctgtgagct gtggtgtagg   2820
ttgcagacgc agctcagatc tggtgttgct gtggctctgg cataggccag cggctacagc   2880
tccgattcaa cccctagcct gggaacctcc atatgccgtg agtgaggccc tagaaaatac   2940
aaaaaacaaa acctgagcag cctgggtgaa aaccaggaat cttagctaga ggctggaagc   3000
agaattgcct tgattcttgc tccctgttga aagcaagaat gtttcaagga gacaaagact   3060
gtaaaaacag gtacaaagtt tattgtcaga gacacagtgt gacatgttgg agagcacaca   3120
gggaagtagt ttatttagga gttcccatca tagctcagtg gttaacgaac ccacctagca   3180
tccatgagga cacaggttcg atccttggcc tcgctcagtg ggttaaggat ccggcattgc   3240
cgtgagctgt ggtgtaggtc acaggctagg attggatctc gagtggctgt ggctgtggtg   3300
tcggccagca gctacagtcc cccagtttga cccctagcct gggaacttcc acatgctgtg   3360
```

-continued

```
cgtgtggccc taaaaagact gaaaaaagaa aaagtagttt atttaagtca gagcaaagca   3420
gtaatccaca cccaaaagag gagtgctggc gttccccccc cgaatgaaga gcgagccaga   3480
gaggtgattt aaaccacttt atagacgggt ctactgggtc tttgtttttc tttgaccagt   3540
tatcctgttt tatttctcac acctgaccag acccagggcc ctccctgatc tgtgtgtgca   3600
gcttttggtc aagatggatt tcagagcaaa gtgttatggg agggcatcag gacctactat   3660
ggcttggtac ccacctccgt tttgacccc caagagtttc tctgtgtata tataactggg   3720
gaggtcttct tgaccccagg agtaattgaa gtagtcagct tatctctcta tactagggag   3780
ttcccatcgt ggctcagtgg taaggaacct gactagtatc cattaggacg caggtttgaa   3840
ccctgtcctc actcagtagg ttaaggatct ggtgttgccg tgagttctgt aggttgcaga   3900
ctcagctggg acctggtgtt gctgtggctg tgatctaggc cggcagcggc agcagcagca   3960
gcagtagctc cgattcaacc cctagcctgg gaacttctat atgccgaggg tgctgcccta   4020
aaaagaaaaa aaaaatcttt ttattccagc agagctcagg tcctgccatt aactttctcc   4080
ttgacatgtc aaaaagaagc aaagcccaaa ttaccaagcc tgacgtgtcc cagctgttct   4140
cagcccaggg gcccatctac ttcctacctc agttcaatga tttcgcatca cacagcaaga   4200
aagttggccc catttcaggt ttcttccaat ctttctgatc acttggagga caagctccat   4260
ctcaaatgtc tccttaatta gtctcttttg acaaggggca cacactgcaa cccgcagtgt   4320
ctttttgtcc agaaatcatc ctgggctccg ggcctggctg gtgacgtccc tgctgcgtga   4380
cccttggcca aggacttagc ctcactgtgc cgtgatcccc tcccctgtta tggggcaaca   4440
gccttggcct tctcagacct tgggcagaat ccagcgccac cgatagaact ttctgtgagg   4500
ctgccccgtg caccagagct gggcagtgtg gctggttcca ccgaagccca gaattcttag   4560
gtttatttcg ctttaactaa ttgaaagtta aatggccacg tgtagttagt ggctcctgca   4620
taggagagag tgccagtcaa ggacctggcc ctgaatggag gccgttcacc catgactaat   4680
gatgtaggaa gtttccctct ttctgtttct ttggtacctt tgcccttggg cacagttttc   4740
agagttgcac tcactgtata gttgccacta tacagacttt ttgtttattt gttgttttta   4800
gattaacaaa tcagtatgtt ctttttaaaa aaagtttatt atagttgatt tacaatgttc   4860
tgtcgattta gatttttaaa tttttttaa tttattttta tttattttat tttatttttt   4920
atttttttatt ttttttgctt ttgagggcca ccccctcggc atatggaggt tcccaggcta   4980
gggggtctag tccgagctgt agccgccagc ctacgccaca gccacagcaa ttcaggatcc   5040
aagccgcgtc tgtgacctac accacagctc acagcaacac tggatcccta acccactgag   5100
caaggtcagg gatcaaaccc gcaacctcat ggttcctagt cagattcgtt aaccactgag   5160
ccacaatggg aactccaaat gttacttttt aagaacaatt agagactttg tctgtgattg   5220
gttctaaaac tgaacacaaa cttggttaat ccccatgcct tgagcaggct tccctcattc   5280
tttacagatg aggaaaccaa ggcacagaaa ggcagagtag ccttctgagg acacacacct   5340
atgaaaacta tacttcccat atgtacccta ctattttagc tgtcgtctga gtgcattttt   5400
cattagagtt aatgctcagt tgtgtttttg ttccttattg caaagatgaa caaatggttt   5460
aaaaataaaa tcatgggaat tcccgctctg gtgcagcggg ttaagaatct gacagcaaca   5520
gctctggtcg ctgtggaggt gcaggttcga tctccagccc tgtgctctgg cttaaggatc   5580
cagcattgct gcagctgtgg cctaggttgc aactgtggct tgcattcgat tcttggccct   5640
gggacttttt ttaatatgcc acaagtgtgg ctattaaaaa aaaaaaaaaa aagaatcatt   5700
ctgggagttt ccttgtgcag gtacaggggt taaggatcca gcatttcact gctatggccc   5760
```

-continued

```
tggttactgc tgtgtcatga gttcactccc tggccccaga atttctgtat gccatagaca   5820
tggccccaaa acacaaaaac acaaaaggat tcttttctat cctgtgagaa accataatgg   5880
aaataaaaag aatatgtgtg ttacagataa aactgagtca ctttacagta cagcagaaat   5940
taacacaatg ttgttaatca actatacttc cttaaaatta aaaaaacacg atcattctaa   6000
atgaaaggaa gcaaaacaaa gcaaaaacag gatcattcta tgtaacagaa attggcacaa   6060
gattgttatt caactttaat aaaaaagttt attataaatt ggctgcaccc aagacatgca   6120
cctgaggcat gtggaagttt ctgcaccata gctgtaacta gagtgagagc agtgacaagg   6180
ccagatcctt acccactgag ccaccaggga actcctgagg gtctgccagc tttttaataa   6240
atttcctggt tttttgtgtt ttattgtttg tgtctttttg ccatttcttg ggccgctcct   6300
atggcatatg gaggttccca ggctaggggt ccaattggag ctgtagccgc cggcctaccc   6360
cagaaccaca gcaacgcggg atccgagcca cgtctgcaac ctacaccaca gctcatggca   6420
atgctggatc cttaacccac tgagcaaggc cagggatcaa acccgcaacc tcacgcttcc   6480
tagttggatt cgttaaccgc tgagccacga cgggaactcc atgaatttcc tgttttgaaa   6540
catgcatgtg aagacaaagc agagagaagt ctaagaaaac ttaatatttg tgtattgccc   6600
atttcttat cttccacact tggctctgcc tctcccagat gtggccacgt gccggcctga   6660
cgagttccag tgctcagacg ggacctgcat ccatggtagc cggcagtgcg acagggaata   6720
tgactgcaag gacctgagcg acgagcaggg ctgtgtcaat ggtgagctct gttccatggg   6780
gtcctgggcc tgggggagat gtggggagga gcctcctggg tcctcactgg ctgtttgtcc   6840
ttggggaaat tagttgacct ctctgagcct cacttctgct tatctgaaaa ctgtgcaaaa   6900
tgaaagccct acctcaggac tgtgagaatg aggtcagagt gtagagagct catatactta   6960
ccctgagtta catgcagata taactccatg taaaaagcac tttgctgaat ctacaacatt   7020
gcagttcctg ttcttgggaa tgatgccagg agaaacttag acctgtgcac tggaggatag   7080
accctggaac aggcagagca gcactgtcct aacagcaaaa cattagaagc aacccaaatg   7140
tttatcagca gtagaattaa tttaattaat ttattttttt ggcttaattt taaggccaca   7200
tccacggcat atggaggttc ccaggctagg ggtctaattg gagctgtagc agccagcctt   7260
caccagagcc acagaaacaa cagatccgag ctgcgtctgc aacctacacc acagcttgca   7320
gcaacgccgg atccttaaac cactgagcga ggctagggtt caaacccatg ccctcacgga   7380
agcttgtcgg gttcactaac tgctgagcca cgacggggac tcccatcttg atttttaagg   7440
gtacggtttg gtaatgccaa gtattcatca ccaccatcca gaactgtttt tatctttcca   7500
aattgaaact ctgtccccat taaccactaa ctccccaagc actgacactt actgtcatac   7560
tttctgtctc tcggaaattg accccttat gaacctcacg tgagtggaat catacagtat    7620
ttgtcttttt gtgacaggct tctttcactt agtataatga cttcaacatg caaccatggt   7680
atagtagaat tcccttcttt tttaagactg aataatattc tattgtatgg atggacattt   7740
gaattgcttc tattccttgg ccattgtgaa taaggctgct gtgaacagag gtgcatggaa   7800
ataattttta aatggcagtg tagtcacaca gtgtagcatc atacagttgg gaatctgagg   7860
ctacagctct cagctgctgc acaggctaaa cctcataaac ttgggcttgg gagcaagaag   7920
caagttgcag gaatttactg gatagttatc acataaggct cagaaacaag cagaattcaa   7980
cagtatattg ttcattcata catgcttgat agaactatta atgaaaaata aggaaatggt   8040
caaatttaag attattattg cctctagggg tagcaggata ggatggcaaa aaccgctgta   8100
attgtctaga ccaggaacag atagtaaaga tcacataata agtattttca gctttgccag   8160
```

```
ccatagtcat aatgacagct gctctactct agtattatag tgtgaaaatc accattgaca   8220

acatatgaac aaatgaacag ggctatatgc caataaacct ttatttaaac aaacaagcag   8280

tgggccagag tttccctgct ctcaatgatg ttctaattct taagctgagt ggaagctcca   8340

ggggtggtga gtaattatgc tgttttatta ccaagtacat ttgcatctat tcttggatca   8400

ataaactatc atattaatca agagcactaa ggaaactcca gctgcccgga agcacctgac   8460

cctcctttgt gactttgata gtg                                           8483
```

<210> SEQ ID NO 3
<211> LENGTH: 4486
<212> TYPE: DNA
<213> ORGANISM: Artificial Sequence
<220> FEATURE:
<223> OTHER INFORMATION: Description of Artificial Sequence: Synthetic LDLR-neo targeting construct

<400> SEQUENCE: 3

```
ctgagccacc atgggaactc ctataatttt tattttatta aataaaatgt aaaggggagc     60

tcgctactca cttttggctg ctcccacagc atgcagaagt tcccaggcca gcgatggaac    120

cctagccaca gcagtgacaa tgccagatcc ttaaccatta ggccaccagg gaactccaag    180

gtttttcct ttgcaaagcc cagactggca aggcaggttg gtcttcctat gagttaaggg    240

tcaatgctgt tttctcccac agtgtctgtc acctgcaaga taggggactt tagctgtggg    300

ggccgtgtca accgctgcat tcctgagtct tggaggtgtg acggtcagca ggactgcgag    360

aatggctcag atgaggaagg ctgttgtaag tggggtccct cacctcgtgg gccatgggcc    420

tcagccacgt ccaagtgacc cgaccagatt ctggtctgag gtcagaattt gttcctccag    480

ctgagagttc cacaaagaaa caaggctgat agtttcagat gggaaggcat gtggcagctg    540

gctctttgat tttattcatt atttataatt tccttttcag ctatataaac tttttttttt    600

ttttttggcc gcatctatgg catgtggaaa ttcctgggcc agggatcaaa cctgtgccac    660

agcagtgaca accctggatc attaacccac tgagccactg ggaactctt gtatagacat    720

gtctttcatg aagtgaggct ctttaaaaaa acaaaaacct ctggacaggt tgtaataacc    780

tataatggga gagaatgtaa aaggaagaga aatatatata tttctctctc tctttttttt    840

atttggtcgc atccactgca tatcaagttc ccaggccagg gactgaattc aaggtgcagc    900

tgcaacccac tgcacagcag tgacaactgc cagatcctta acctgctgaa cgaccaggga    960

actccctctt tttcatgttc ttttccatta tagtttatta caagaaattg aatgtggatc   1020

cctgtgcaaa ctcttaaata gtgcttccca tgtgcccagc ccaacctggg aactttacac   1080

acgttcctca cagtaacacc ttgagacacg aacagacgtc cgaggcattg agagggccgg   1140

gagctgggtg ggtatctggg tggggcagtg gttccaaatc cagggcccct gactactacc   1200

ccaggtccac tcactgggct tggcctgtcc tgggctcagt gtccccatct atgcagtggg   1260

ctggtgtagg gcctccccgg taacctggct gtgatcttct gtctatttct gaagccccca   1320

agacgtgctc ccaagatgag ttccgctgcc aggacggcaa gtgcatcgcc ccaaagtttg   1380

tctaggatat ctgcagaatt cggcttgtac tgataacttc gtatagcata cattatacga   1440

agttgttgcc tgctattgtc ttcccaatcc tccccttgc tgtcctgccc caccccaccc   1500

cccagaatag aatgacacct actcagacaa tgcgatgcaa tttcctcatt ttattaggaa   1560

aggacagtgg gagtggcacc ttccagggtc aaggaaggca cgggggaggg gcaaacaaca   1620

gatggctggc aactagaagg cacagtcgag gctgatcagc gagctctaga gaattgatcc   1680
```

```
cctcagaaga actcgtcaag aaggcgatag aaggcgatgc gctgcgaatc gggagcggcg   1740
ataccgtaaa gcacgaggaa gcggtcagcc cattcgccgc caagctcttc agcaatatca   1800
cgggtagcca acgctatgtc ctgatagcgg tccgccacac ccagccggcc acagtcgatg   1860
aatccagaaa agcggccatt ttccaccatg atattcggca agcaggcatc gccatgggtc   1920
acgacgagat cctcgccgtc gggcatgcgc gccttgagcc tggcgaacag ttcggctggc   1980
gcgagcccct gatgctcttc gtccagatca tcctgatcga caagaccggc ttccatccga   2040
gtacgtgctc gctcgatgcg atgtttcgct tggtggtcga atgggcaggt agccggatca   2100
agcgtatgca gccgccgcat tgcatcagcc atgatggata ctttctcggc aggagcaagg   2160
tgagatgaca ggagatcctg ccccggcact tcgcccaata gcagccagtc ccttcccgct   2220
tcagtgacaa cgtcgagcac agctgcgcaa ggaacgcccg tcgtggccag ccacgatagc   2280
cgcgctgcct cgtcctgcag ttcattcagg gcaccggaca ggtcggtctt gacaaaaaga   2340
accgggcgcc cctgcgctga cagccggaac acggcggcat cagagcagcc gattgtctgt   2400
tgtgcccagt catagccgaa tagcctctcc acccaagcgg ccggagaacc tgcgtgcaat   2460
ccatcttgtt caatggccga tcccatattg gctgcaggtc gaaaggcccg gagatgagga   2520
agaggagaac agcgcggcag acgtgcgctt ttgaagcgtg cagaatgccg ggcctccgga   2580
ggaccttcgg gcgcccgccc cgcccctgag cccgcccctg agcccgcccc cggacccacc   2640
ccttcccagc ctctgagccc agaaagcgaa ggagcaaagc tgctattggc cgctgcccca   2700
aaggcctacc cgcttccatt gctcagcggt gctgtccatc tgcacgagac tagtgagacg   2760
tgctacttcc atttgtcacg tcctgcacga cgcgagctgc ggggcggggg ggaacttcct   2820
gactagggga ggagtagaag gtggcgcgaa ggggccacca aagaacggag ccggttggcg   2880
cctaccggtg gatgtggaat gtgtgcgagg ccagaggcca cttgtgtagc gccaagtgcc   2940
cagcggggct gctaaagcgc atgctccaga ctgccttggg aaaagtactg ataacttcgt   3000
atagcataca ttatacgaag ttgttgaagc cgaattccag cacactggcg gccgttacta   3060
gtggatccga gctcggtacc aagcttgact cggaccggga ctgcctggac ggctcggatg   3120
aagcatcctg ccccacaccc acctgtggcc ccgccagctt ccagtgcaac agctccacct   3180
gcatccctga gctgtgggcc tgtgatggtg atcctgactg cgaggacggc tcagacgagt   3240
ggccacagca ctgcaggagc cacagctcat cactccccga gaggagcaac aacccctgct   3300
cagccctcga gttccactgc cacagtggcg agtgcatcca ctccagctgg cgctgcgacg   3360
gagacactga ctacaaggac aagtctgacg aggagaactg cggtaggggc gccttgggga   3420
tcccttcacc tgtccctggg ccctcctgtg tggggggtgg ggggctggcc agtgccttta   3480
ggtggttctg atcttggaga gacagctgtg agtgatggct cgaagcaaga tcttaattct   3540
ctgctcggga atcaaacctg ggcagcctgg gtgttccgtg gtggctcagt ggttaacgaa   3600
tctgactagg aaccatgagg ttgcaggttc gatccctggc cttgctcagt gggttaagga   3660
tctggtgttg ctgtgagctg tggtgtaggt tgcagacgca gctcagatct ggtgttgctg   3720
tggctctggc ataggccagc ggctacagct ccgattcaac ccctagcctg ggaacctcca   3780
tatgccgtga gtgaggccct agaaaataca aaaaacaaaa cctgagcagc ctgggtgaaa   3840
accaggaatc ttagctagag gctggaagca gaattgcctt gattcttgct ccctgttgaa   3900
agcaagaatg tttcaaggag acaaagactg taaaaacagg tacaaagttt attgtcagag   3960
acacagtgtg acatgttgga gagcacacag ggaagtagtt tatttaggag ttcccatcat   4020
agctcagtgg ttaacgaacc cacctagcat ccatgaggac acaggttcga tccttggcct   4080
```

-continued

```
cgctcagtgg gttaaggatc cggcattgcc gtgagctgtg gtgtaggtca caggctagga   4140

ttggatctcg agtggctgtg gctgtggtgt cggccagcag ctacagtccc ccagtttgac   4200

ccctagcctg ggaacttcca catgctgtgc gtgtggccct aaaaagactg aaaaaagaaa   4260

aagtagttta tttaagtcag agcaaagcag taatccacac ccaaaagagg agtgctggcg   4320

ttcccccccc gaatgaagag cgagccagag aggtgattta aaccacttta tagacgggtc   4380

tactgggtct ttgtttttct ttgaccagtt atcctgtttt atttctcaca cctgaccaga   4440

cccagggccc tccctgatct gtgtgtgcag cttttggtca agatgg                  4486
```

```
<210> SEQ ID NO 4
<211> LENGTH: 845
<212> TYPE: PRT
<213> ORGANISM: Sus scrofa

<400> SEQUENCE: 4

Met Lys Ser Thr Gly Trp Val Leu Arg Trp Ala Val Ala Leu Leu Ile
1               5                   10                  15

Ala Ala Val Ala Ala Ala Val Glu Glu Lys Cys Gly Arg Asn Glu Phe
            20                  25                  30

Gln Cys Arg Asp Gly Lys Cys Ile Ser Tyr Lys Trp Ile Cys Asp Gly
        35                  40                  45

Asn Thr Glu Cys Lys Asp Gly Ser Asp Glu Ser Leu Glu Thr Cys Met
    50                  55                  60

Ser Val Thr Cys Lys Ile Gly Asp Phe Ser Cys Gly Gly Arg Val Asn
65                  70                  75                  80

Arg Cys Ile Pro Glu Ser Trp Arg Cys Asp Gly Gln Gln Asp Cys Glu
                85                  90                  95

Asn Gly Ser Asp Glu Glu Gly Cys Ser Pro Lys Thr Cys Ser Gln Asp
            100                 105                 110

Glu Phe Arg Cys Gln Asp Gly Lys Cys Ile Ala Pro Lys Phe Val Cys
        115                 120                 125

Asp Ser Asp Arg Asp Cys Leu Asp Gly Ser Asp Glu Ala Ser Cys Pro
    130                 135                 140

Thr Pro Thr Cys Gly Pro Ala Ser Phe Gln Cys Asn Ser Ser Thr Cys
145                 150                 155                 160

Ile Pro Glu Leu Trp Ala Cys Asp Gly Asp Pro Asp Cys Glu Asp Gly
                165                 170                 175

Ser Asp Glu Trp Pro Gln His Cys Arg Ser His Ser Ser Ser Leu Pro
            180                 185                 190

Glu Arg Ser Asn Asn Pro Cys Ser Ala Leu Glu Phe His Cys His Ser
        195                 200                 205

Gly Glu Cys Ile His Ser Ser Trp Arg Cys Asp Gly Asp Thr Asp Cys
    210                 215                 220

Lys Asp Lys Ser Asp Glu Glu Asn Cys Asp Val Ala Thr Cys Arg Pro
225                 230                 235                 240

Asp Glu Phe Gln Cys Ser Asp Gly Thr Cys Ile His Gly Ser Arg Gln
                245                 250                 255

Cys Asp Arg Glu Tyr Asp Cys Lys Asp Met Ser Asp Glu Gln Gly Cys
            260                 265                 270

Val Asn Ala Thr Leu Cys Glu Gly Pro Asn Lys Phe Lys Cys Gln Ser
        275                 280                 285

Gly Glu Cys Ile Ser Leu Asp Lys Val Cys Asn Ser Val Arg Asp Cys
    290                 295                 300
```

-continued

```
Arg Asp Trp Ser Asp Glu Pro Leu Lys Glu Cys Gly Thr Asn Glu Cys
305                 310                 315                 320

Leu Asp Asn Lys Gly Gly Cys Ser His Ile Cys Asn Asp Leu Lys Ile
                325                 330                 335

Gly Tyr Glu Cys Leu Cys Pro Glu Gly Phe Gln Leu Val Asp Lys His
            340                 345                 350

Arg Cys Glu Asp Ile Asp Glu Cys Gln Asp Pro Asp Ala Cys Ser Gln
        355                 360                 365

Ile Cys Val Asn Leu Glu Gly Ser Tyr Lys Cys Gln Cys Glu Glu Gly
    370                 375                 380

Phe Gln Leu Glu Pro Leu Thr Lys Ala Cys Lys Ala Ile Gly Thr Ile
385                 390                 395                 400

Ala Tyr Leu Phe Phe Thr Asn Arg His Glu Val Arg Lys Met Thr Leu
                405                 410                 415

Asp Arg Ser Glu Tyr Thr Ser Leu Ile Pro Asn Leu Lys Asn Val Val
            420                 425                 430

Ala Leu Asp Thr Glu Val Ala Ser Asn Arg Ile Tyr Trp Ser Asp Leu
        435                 440                 445

Ser Gln Arg Lys Ile Tyr Ser Thr Gln Ile Asp Arg Ala Pro Ser Phe
    450                 455                 460

Ser Ser Tyr Asp Thr Ile Ile Gly Glu Asp Leu Gln Ala Pro Asp Gly
465                 470                 475                 480

Leu Ala Val Asp Trp Ile His Ser Asn Ile Tyr Trp Thr Asp Ser Ile
                485                 490                 495

Leu Gly Thr Val Ser Val Ala Asp Thr Lys Gly Val Lys Arg Lys Thr
            500                 505                 510

Leu Phe Gln Glu Lys Gly Ser Lys Pro Arg Ala Ile Val Val Asp Pro
        515                 520                 525

Val His Gly Phe Met Tyr Trp Thr Asp Trp Gly Thr Pro Ala Lys Ile
    530                 535                 540

Lys Lys Gly Gly Leu Asn Gly Val Asp Val Tyr Ser Leu Val Thr Glu
545                 550                 555                 560

Asp Ile Gln Trp Pro Asn Gly Ile Thr Leu Asp Leu Ser Gly Gly Arg
                565                 570                 575

Leu Tyr Trp Val Asp Ser Lys Leu His Ser Ile Ser Ser Ile Asp Val
            580                 585                 590

Asn Gly Gly Asn Arg Lys Thr Val Leu Glu Asp Lys Thr Lys Leu Ala
        595                 600                 605

His Pro Phe Ser Leu Ala Ile Phe Glu Asp Lys Val Phe Trp Thr Asp
    610                 615                 620

Ile Ile Asn Glu Ala Ile Phe Ser Ala Asn Arg Leu Thr Gly Ser Asp
625                 630                 635                 640

Ile His Leu Met Ala Glu Asn Leu Leu Ser Pro Glu Asp Ile Val Leu
                645                 650                 655

Phe His Asn Leu Thr Gln Pro Arg Gly Val Asn Trp Cys Glu Arg Thr
            660                 665                 670

Ala Leu Gln Asn Gly Gly Cys Gln Tyr Leu Cys Leu Pro Ala Pro Gln
        675                 680                 685

Ile Asn Pro Arg Ser Pro Lys Phe Thr Cys Ala Cys Pro Asp Gly Met
    690                 695                 700

Leu Leu Ala Lys Asp Met Arg Ser Cys Leu Thr Glu Thr Glu Pro Ala
705                 710                 715                 720
```

-continued

```
Gly Thr Thr Gln Gly Pro Ser Met Val Asn Ser Thr Ala Val Gly Pro
                725                 730                 735

Lys His Thr Ala Ser Ser Glu Leu Thr Thr Ala Glu Ser Val Thr Met
            740                 745                 750

Ser Gln His Ala Leu Gly Asp Val Ala Gly Arg Gly Val Thr Glu Lys
        755                 760                 765

Pro Gln Ser Val Gly Ala Leu Tyr Ile Val Leu Pro Ile Ala Leu Leu
    770                 775                 780

Ile Leu Leu Phe Phe Gly Thr Phe Leu Leu Trp Lys Asn Trp Arg Leu
785                 790                 795                 800

Lys Ser Ile Asn Ser Ile Asn Phe Asp Asn Pro Val Tyr Gln Lys Thr
                805                 810                 815

Thr Glu Asp Glu Val His Ile Cys Arg Ser Gln Asp Gly Tyr Thr Tyr
            820                 825                 830

Pro Ser Arg Gln Met Val Ser Leu Glu Asp Asp Val Ala
        835                 840                 845


<210> SEQ ID NO 5
<211> LENGTH: 860
<212> TYPE: PRT
<213> ORGANISM: Homo sapiens

<400> SEQUENCE: 5

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255
```

```
Arg Glu Tyr Asp Cys Lys Asp Met Ser Asp Glu Val Gly Cys Val Asn
        260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670
```

-continued

```
Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860
```